United States Patent [19]
Cynshi et al.

[11] Patent Number: 6,133,279
[45] Date of Patent: Oct. 17, 2000

[54] THERAPEUTIC AGENTS FOR RENAL DISEASES AND ORGAN PRESERVATIVES

[75] Inventors: Osamu Cynshi; Yoshiaki Takashima; Kunio Tamura; Akira Ishikawa; Yoshiaki Kato, all of Shizuoka-ken, Japan

[73] Assignee: Chugai Seiyaku Kabushiki Kaisha, Tokyo, Japan

[21] Appl. No.: 09/202,593
[22] PCT Filed: May 23, 1997
[86] PCT No.: PCT/JP97/01729
  § 371 Date: Dec. 17, 1998
  § 102(e) Date: Dec. 17, 1998
[87] PCT Pub. No.: WO97/49388
  PCT Pub. Date: Dec. 31, 1997

[30] Foreign Application Priority Data

Jun. 26, 1996 [JP] Japan .................................. 8-200917

[51] Int. Cl.[7] .................... A61K 31/085; A61K 31/22; A61K 31/34; A61K 31/38; C07D 307/79
[52] U.S. Cl. .................... 514/278; 514/422; 514/432; 514/443; 514/469; 514/546; 514/731; 514/733; 514/734; 546/17; 548/525; 549/13; 549/51; 549/344; 549/345; 549/462; 560/130; 560/138; 568/644; 568/650
[58] Field of Search .............................. 546/17; 548/525; 549/13, 51, 344, 345, 462; 560/130, 138; 568/644, 650; 514/278, 442, 432, 443, 469, 546, 731, 733, 734

[56] References Cited

U.S. PATENT DOCUMENTS 5,574,178 11/1996 Tamura et al. ......................... 549/462
5,789,436 8/1998 Kato et al. ............................. 514/443

FOREIGN PATENT DOCUMENTS 9408931 4/1994 WIPO.
9527710 10/1995 WIPO.
9717066 5/1997 WIPO.

OTHER PUBLICATIONS

Mabile et al., "Tocopherol and Trolox block the early intracellular events (Tbars and Calcium Rises) elicited by oxidized low density lipoproteins in cultured endothelial cells", *Free Radical Biology & Medicine*, vol. 19 No. 2, pp. 177–187, (1995).
Agarwal et al., "Renal tubular epithelial cells mimic endothelial cells upon exposure to oxidized LDL" *American Physiological Society*, 271:F814–F823, (1996).
Drukker et al., "Failure of Antioxidant Therapy to Attenuate Interstitial Disease in Rats with Reversible Nephrotic Syndrome", *Journal of the American Society of Nephrology*, 9:243–25$_1$, (1998).
Lee et al., "Dietary antioxiant inhibits lipoprotein oxidation and renal injury in experimental focal segmental glomerulosclerosis", *Kidney International*, 51:1151–1159, (1997).
Hirano et al., "The Lowering Effect of Probucol on Plasma Lipoprotein and Proteinuria in Puromycin Aminocucleoside–Induced Nephrotic Rats", *Nephron*, 58:95–100, (1991).
Thakur et al., "Evidence suggesting a role for hydroxyl radical in puromycin aminonucleoside–induced proteinuria", *Kidney International*, 34:494–499, (1988).
Paller et al., "Oxygen Free Radicals in Ischemic Acute Renal Failure in the Rat", *J. Clin. Invest.*, 74:1156–1164, (1994).
Rehan et al., "Evidence for the Role of Oxygen Radicals in Acute Nephrotoxic Nephritis", *Laboratory Investigations*, vol. 51, No. 4, pp. 396–403, (1984).
Modi et al., "Effect of probulcol in renal function and structure in rats with subtotal kidney ablation" *J. Lab. Clin. Med.*, vol. 120, No. 2, pp. 310–317, (1992).
Branden et al., "Effect of Vitamin E on Antioxidant Enzymes, Lipid Proxidatiion Products and Glomerulosclerosis in the Rat Remnant Kidney", *Nephron*, 76:77–81, (1997).
Konya et al., "Lack of effect of antioxidant therapy during renal ischemia and reperfusion in dogs" *Experientia*, 49:235–237, (1993).
Holding et al., "Failure of a 21–Aminosteriod Antixoxidant to Ameliorate Cisplatin–Induced Nephrotoxicity" *Human & Experimental Toxicology*, 10:323–326, (1991).

*Primary Examiner*—Fiona T. Powers
*Attorney, Agent, or Firm*—Browdy and Neimark

[57] ABSTRACT

Herein disclosed are therapeutic agents for renal diseases and organ preservatives containing a compound represented by the general formula (1):

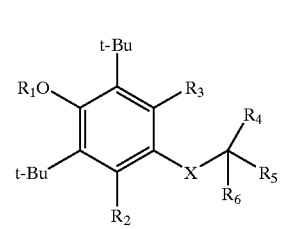

(1)

wherein X represents an oxygen atom or a group represented by the general formula (2):

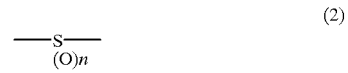

(2)

where n represents an integer from 0 to 2, $R_1$ represents a hydrogen atom or an acyl group, $R_2$ represents a hydrogen atom, a lower alkyl group or a lower alkenyl group, $R_3$ represents a lower alkyl group, $R_4$, $R_5$ and $R_6$, which may be the same or different, each represents a hydrogen atom or an optionally substituted alkyl group, and $R_6$ further represents a formyl, carboxyl, lower alkoxycarbonyl or optionally substituted carbamoyl group, or $R_3$ and $R_4$ may be taken together to form a five-membered ring, or $R_5$ and $R_6$ may be taken together to form a cycloalkyl group, provided that when the five-membered ring formed by $R_3$ and $R_4$ and the benzene ring form benzofuran or benzo[b]thiophene, $R_6$ is absent.

38 Claims, No Drawings

THERAPEUTIC AGENTS FOR RENAL DISEASES AND ORGAN PRESERVATIVES

FIELD OF THE INVENTION

The present invention relates to therapeutic agents for renal diseases or organ preservatives. More specifically, it relates to therapeutic agents, which contain a 2,6-di-t-butylphenol derivative as an active ingredient, for renal diseases such as chronic renal failure, diabetic nephropathy, glomerular nephritis, immunocomplex nephritis, acute renal failure, nephropathies caused by platinum complex-based anticancer agents such as cisplatin or other drugs such as gentamicin, nephropathies caused by agrichemicals such as Paracort, uremia, etc. or organ preservatives.

BACKGROUND ART

Kidney is one of organs involving potential oxidative stress in the living organism. The importance of radical injury caused by active oxygen species or free radicals has long been pointed out in the formation and progression of various renal diseases such as acute renal failure, drug-induced nephropathies, glomerular nephritis, diabetic nephropathy, chronic renal failure, and renal transplantation. In recent years, the role of lipids in cell injury has attracted particular attention (Keane W. F., Lipids and the kidney. Kidney Int., 46:910–920, 1994; Higuchi and Sanaka, "Renal Diseases", Antioxidants—Free radicals and biological defense (Niki, Shimazaki and Mino, eds.) Gakkai Shuppan Center, 223–229, 1994; Aoyagi "Therapy with Antioxidants/Scavenger, No. 3, Renal Diseases", Biomedicine & Therapeutics, 26:592–596, 1992). However, the effect of antioxidants, particularly inhibitors against lipid peroxidation has not been well explained on renal diseases, and no useful compound that inhibits the lipid peroxidation has been reported as a therapeutic or preventive agent or organ preservative.

Vitamin E (α-tocopherol) is a natural potent inhibitor against lipid peroxidation and its use in renal transplantation and renal ischemic models has been reported (Marubayashi, Dohi and Kawasaki "Renal maintenance and active oxygen species", Kidney and Dialysis, 24:785–790, 1988; Takenaka M., Tatsukawa Y., Dohi K., Ezaki H., Matsukawa K., Kawasaki T., Transplantation, 32:137–141, 1981), but its effect is not sufficient. This is because it acts on only the surfaces of membranes and lipid and can not show inhibitory effect against lipid peroxidation in the deep inside of membranes and lipids (Niki E., Chem. Phys. Lipids, 44:227–253, 1987). Because Vitamin E endogenously exists in a significant amount (Nakamura "Absorption, Distribution and Excretion of Vitamin E", Vitamin E—Basic and Clinical Study (Igarashi, eds.), Ishiyaku Shuppan, 33–58, 1985), the endogenous Vitamin E is expected to have an inhibitory effect against lipid peroxidation near the surfaces of membranes and lipid. On the other hand, an insufficient protection mechanism against lipid peroxidation exists in the deep inside of membranes and lipids and, therefore, the inhibition of lipid peroxidation in the deep inside of membranes and lipids seems to be important for treatment and prevention of renal diseases. Additionally, the effects of probucol, one of lipid-soluble antioxidants, have been reported on various renal disease models (Modi K. S., Schreiner G. F., Purkerson M. L., J. Lab. Clin. Med., 120:310–317, 1992; Bird J. E., Milhoan K., Wilson C. B., Young S. G., Mundy C. A., Parthasarathy S., Blantz R. C., J. Clin. Invest., 81:1630–1638, 1988; Hirano T., Mamo J. C. L., Nagano S., Sugisaki T., Nephron, 58:95–100, 1991). However, the simple phenolic compounds such as probucol and butylated hydroxytoluene have a 10 or 100 fold lower reactivity with lipid peroxyl radicals than α-tocopherol (Gotoh N., Shimizu K., Komuro E., Tsuchiya J., Noguchi N., Niki E., Biochem. Biophys. Acta, 1128:147–154, 1992; Burton G. W., Ingold K. U., J. Am. Chem. Soc., 103:6472–6477, 1981). Thus, probucol has not shown sufficient protective effect for renal functions.

Thus, a potent cytoprotective agent that inhibits the lipid peroxidation hardly inhibited by Vitamin E is expected to be effective for the prevention and treatment of various renal diseases and preservation of organs, but any such agent has not been reported.

DISCLOSURE OF THE INVENTION

As a result of extensive research to solve the above problems, we found that compounds represented by the general formula (1):

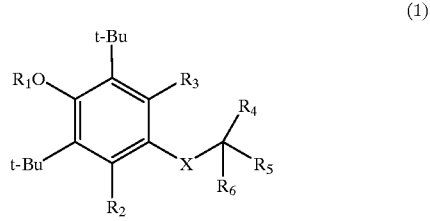

wherein X represents an oxygen atom or a group represented by the general formula (2):

wherein n represents an integer from 0 to 2, $R_1$ represents a hydrogen atom or an acyl group, $R_2$ represents a hydrogen atom, a lower alkyl group or a lower alkenyl group, $R_3$ represents a lower alkyl group, and $R_4$, $R_5$ and $R_6$, which may be the same or different, each represents a hydrogen atom, an optionally substituted alkyl group, an optionally substituted alkenyl group, an optionally substituted alkynyl group or an optionally substituted aryl group, and $R_6$ further represents a formyl group, a carboxyl group, a lower alkoxycarbonyl group or an optionally substituted carbamoyl group, or $R_3$ and $R_4$ may be taken together to form a five-membered ring, or $R_5$ and $R_6$ may be taken together to form a cycloalkyl group or a saturated heterocyclic group containing one or more oxygen atoms, sulfur atoms or alkyl-substituted nitrogen atoms, provided that when the five-membered ring formed by $R_3$ and $R_4$ and the benzene ring are taken together to form benzofuran, benzo[b]thiophene, benzo[b]thiophene-1-oxide or benzo[b]thiophene-1,1-dioxide, $R_6$ is absent, or optically active isomers or pharmaceutically acceptable salts thereof show a potent cytoprotective effect on kidney-derived cells as well as a potent improving effect on renal functions in puromycin-induced nephropathy and ischemic active renal failure models, and thus attained the present invention.

Some of compounds represented by the general formula (1) have already been disclosed in patent publications (JP 6-206842/94, WO94/08930, JP 7-330759/95, WO95/27710).

PREFERRED EMBODIMENT OF THE INVENTION

In the definition of compounds represented by the general formula (I), the acyl group for $R_1$ includes acetyl, formyl, propionyl, benzoyl, benzyloxycarbonyl, aminoacetyl, N-methylaminoacetyl and N,N-dimethylaminoacetyl groups. The lower alkyl group for $R_2$ means a straight or branched alkyl group having 1 to 6 carbon atoms, for example, a methyl, ethyl, n-propyl, i-propyl, n-butyl, s-butyl or t-butyl group. The lower alkenyl group means a straight or branched alkenyl group having 2 to 6 carbon atoms, for example, a vinyl, allyl, butenyl, or pentenyl group.

The alkyl group for $R_4$, $R_5$ and $R_6$ means a straight or branched alkyl group having 1 to 20 carbon atoms, for example, a methyl, ethyl, n-propyl, i-propyl, n-butyl, s-butyl, t-butyl, pentyl, hexyl, heptyl, octyl, nonyl or decyl group. The alkenyl group means a straight or branched alkenyl group having 2 to 20 carbon atoms, for example, a vinyl, allyl, butenyl, pentenyl, geranyl or farnesyl group. The alkynyl group means a straight or branched alkynyl group having 2 to 20 carbon atoms, for example, an ethynyl, propynyl or butynyl group. The aryl group means a monovalent substituent obtained by removing a hydrogen atom from an aromatic hydrocarbon, for example, a phenyl, tolyl, xylyl, biphenyl, naphthyl, anthryl or phenanthryl group.

The substituents of the optionally substituted alkyl group, optionally substituted alkenyl group, optionally substituted alkynyl group and optionally substituted aryl group include a halogen atom, a lower alkyl group, a lower alkenyl group, a hydroxy group, an amino group, a substituted amino group such as dimethylamino, an alkoxy group, an aryloxy group such as 3,5-di-t-butyl-4-hydroxy-2-methylphenoxy, a nitro group, a trifluoromethyl group, a phenyl group and an acetoxy group. The halogen atom includes chlorine, bromine, fluorine and iodine. The lower alkyl and lower alkenyl groups include those listed above for $R_2$. The alkoxy group includes alkyloxy groups derived from alkyl groups listed above for $R_4$, $R_5$ and $R_6$.

The five-membered ring formed by $R_3$ and $R_4$ includes a furan ring, a dihydrofuran ring, a thiophene ring, and a dihydrothiophene ring, which together with the benzene ring in the general formula (1) form a benzofuran ring, a dihydrobenzofuran ring, a benzo[b]thiophene ring and a dihydrobenzothiophene ring, respectively.

The cycloalkyl group formed by $R_5$ and $R_6$ means a cycloalkyl group having 3 to 8 carbon atoms, for example, a cyclopropyl, cyclobutyl, cyclopentyl, cyclohexyl, cycloheptyl or cyclooctyl group. The saturated heterocyclic group containing one or more oxygen atoms, sulfur atoms or alkyl-substituted nitrogen atoms includes tetrahydropyranyl, tetrahydrothiopyranyl and N-methylpiperidyl groups.

$R_6$ further represents a formyl, carboxyl, lower alkoxycarbonyl or optionally substituted carbamoyl group. The lower alkoxycarbonyl group includes, for example, methoxycarbonyl, ethoxycarbonyl, propoxycarbonyl, isopropoxycarbonyl, butoxycarbonyl and t-butoxycarbonyl groups. The optionally substituted carbamoyl group includes mono- or di-lower alkyl-substituted carbamoyl groups as well as cyclic aminocarbonyl groups. The mono- or di-lower alkyl-substituted carbamoyl group means a carbamoyl group substituted by one or more lower alkyl groups such as methyl and ethyl, and includes, for example, N-methylcarbamoyl, N-ethylcarbamoyl, N,N-dimethylcarbamoyl and N,N-diethylcarbamoyl groups. The cyclic aminocarbonyl group means a di-lower alkyl-substituted carbamoyl group in which the two organic groups attached to the nitrogen atom together form a ring, including, for example, pyrrolidinocarbonyl, piperidinocarbonyl, piperazinocarbonyl and morpholinocarbonyl groups.

When X is an oxygen atom in the general formula (1), the following substituents are preferred.

$R_1$ is preferably a hydrogen atom, an acetyl, benzyloxycarbonyl, aminoacetyl, N-methylaminoacetyl or N,N-dimethylaminoacetyl group, especially a hydrogen atom, an acetyl or N,N-dimethylaminoacetyl group.

$R_2$ is preferably a hydrogen atom, a methyl or n-propyl group, especially a hydrogen atom.

Preferably, $R_3$ and $R_4$ are taken together to form a furan or dihydrofuran ring, especially a dihydrofuran ring.

$R_5$ is preferably a hydrogen atom or a methyl, ethyl, n-propyl, i-propyl, n-butyl, i-butyl, s-butyl, t-butyl, n-pentyl, benzyl, hydroxymethyl, aminomethyl or N,N-dimethylaminomethyl group, especially a hydrogen atom or a methyl, n-pentyl, benzyl, hydroxymethyl, aminomethyl or N,N-dimethylaminomethyl group.

$R_6$ is preferably a hydrogen atom or a methyl, ethyl, n-propyl, i-propyl, n-butyl, i-butyl, s-butyl, t-butyl, n-pentyl, benzyl, cyanomethyl, methoxycarbonyl, pyrrolydinocarbonyl, 2-ethoxycarbonylethyl, 2-ethoxycarbonylethenyl, 3-aminoguanidinomethyl or N-guanidinoaminomethyl group, especially a hydrogen atom or a methyl, n-pentyl, benzyl, methoxycarbonyl, pyrrolidinocarbonyl, 3-aminoguanidinomethyl or N-guanidinoamineohtyl group.

The ring formed by $R_5$ and $R_6$ is preferably a cyclopentyl, cyclohexyl, cycloheptyl, cyclooctyl, tetrahydropyranyl, tetrahydrothiopyranyl or N-methylpiperidyl group, especially a cyclopentyl, cyclohexyl, cycloheptyl or tetrahydropyranyl group.

When X in the general formula (1) is a group of the general formula (2):

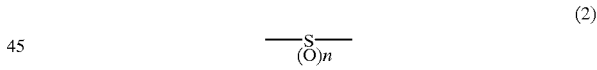

where n represents an integer of 0 to 2, the following substituents are preferred.

$R_1$ is preferably a hydrogen atom or an acetyl, benzyloxycarbonyl, aminoacetyl, N-methylaminoacetyl or N,N-dimethylaminoacetyl group, especially a hydrogen or an acetyl or N,N-dimethylaminoacetyl group.

$R_2$ is preferably a hydrogen atom or a methyl or n-propyl group, especially a hydrogen atom.

Preferably, $R_3$ and $R_4$ are taken together to form a thiophene or dihydrothiophene ring, especially a dihydrothiophene ring.

$R_5$ is preferably a hydrogen atom or a methyl, ethyl, n-propyl, i-propyl, n-butyl, i-butyl, s-butyl, t-butyl, n-pentyl, hydroxymethyl, aminomethyl or N,N-dimethylaminomethyl group, especially a hydrogen atom or a methyl, hydroxymethyl, aminomethyl or N,N-dimethylaminomethyl group.

$R_6$ is preferably a hydrogen atom or a methyl, ethyl, n-propyl, i-propyl, n-butyl, i-butyl, s-butyl, t-butyl, n-pentyl, benzyl, cyanomethyl, methoxycarbonyl, pyrrolydinocarbonyl, 2-ethoxycarbonylethyl, 2-ethoxycarbonylethenyl, 3-aminoguanidinomethyl or N-guanidinoaminomethyl group, especially a hydrogen atom or a methyl or n-pentyl group.

The ring formed by $R_5$ and $R_6$ is preferably a cyclopentyl, cyclohexyl, cycloheptyl, cyclooctyl, tetrahydropyranyl, tetrahydrothiopyranyl or N-methylpiperidyl group, especially a cyclopentyl, cyclohexyl, cycloheptyl or tetrahydropyranyl group.

n is preferably 0 or 1, especially 0.

Preferred examples of the compound represented by the general formula (1) are represented by the general formula (3):

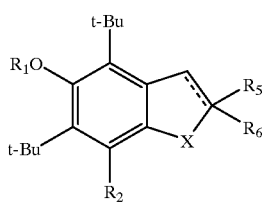

(3)

wherein X represents an oxygen atom or a group represented by the general formula (2):

(2)

where n represents an integer from 0 to 2, $R_1$ represents a hydrogen atom or an acyl group, $R_2$ represents a hydrogen atom, a lower alkyl group or a lower alkenyl group, and $R_5$ and $R_6$, which may be the same or different, each represents a hydrogen atom, an optionally substituted alkyl group, an optionally substituted alkenyl group, an optionally substituted alkynyl group or an optionally substituted aryl group, and $R_6$ further represents a formyl group, a carboxyl group, a lower alkoxycarbonyl group or an optionally substituted carbamoyl group, or $R_5$ and $R_6$ may be taken together to form a cycloalkyl group or a saturated heterocyclic group containing one or more oxygen atoms, sulfur atoms or alkyl-substituted nitrogen atoms, provided that when the bicyclic ring containing X is benzofuran, benzo[b]thiophene, benzo[b]thiophene-1-oxide or benzo[b]thiophene-1,1-dioxide, $R_6$ is absent.

The definition and preferred examples of each substituent in the general formula (3) are as mentioned for the general formula (1).

Another preferred examples of the compound represented by the general formula (1) are represented by the general formula (4):

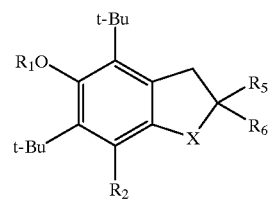

(4)

wherein X represents an oxygen atom or a sulfur atom, $R_1$ represents a hydrogen atom or an acyl group, $R_2$ represents a hydrogen atom, a lower alkyl group or a lower alkenyl group, and $R_5$ and $R_6$, which may be the same or different, each represents a hydrogen atom, an optionally substituted alkyl group having 1 to 20 carbon atoms, an optionally substituted alkenyl group having 2 to 20 carbon atoms, an optionally substituted alkynyl group having 2 to 20 carbon atoms or an optionally substituted aryl group, and $R_6$ further represents a formyl group, a carboxyl group, a lower alkoxycarbonyl group or an optionally substituted carbamoyl group, or $R_5$ and $R_6$ may be taken together to form a cycloalkyl group or a saturated heterocyclic group containing one or more oxygen atoms, sulfur atoms or alkyl-substituted nitrogen atoms.

The definition and preferred examples of each substituent in the general formula (4) are as mentioned for the general formula (1). In addition, $R_6$ may represent (i) a formyl, carboxyl, lower alkoxycarbonyl, carbamoyl, mono- or di-lower alkyl-substituted carbamoyl, pyrrolydinocarbonyl, piperidinocarbonyl, piperazinocarbonyl or morpholinocarbonyl group; (ii) an alkyl group having 1 to 20 carbon atoms which is substituted by one or more substituents selected from the group consisting of cyano, carboxyl, lower alkoxycarbonyl, carbamoyl, mono- or di-lower alkyl-substituted carbamoyl, pyrrolydinocarbonyl, piperidinocarbonyl, piperazinocarbonyl and morpholinocarbonyl groups; or (iii) an alkenyl group having 2 to 20 carbon atoms which is substituted by one or more substituents selected from the group consisting of cyano, carboxyl, lower alkoxycarbonyl, carbamoyl, mono- or di-lower alkyl-substituted carbamoyl, pyrrolydinocarbonyl, piperidinocarbonyl, piperazinocarbonyl and morpholinocarbonyl groups. Moreover, $R_6$ may represent (i) an alkyl group having 1 to 20 carbon atoms which is substituted by one or more substituents selected from the group consisting of thioureido, 3-aminoguanidino, N-guanidinoamino, 4-guanidinophenoxy and 4-(N-guanidinoaminomethyl) phenoxy groups; or (ii) an alkenyl group having 2 to 20 carbon atoms which is substituted by one or more substituents selected from the group consisting of thioureido, 3-aminoguanidino, N-guanidinoamino, 4-guanidinophenoxy and 4-(N-guanidinoaminomethyl) phenoxy groups.

Compounds of the general formula (1) of the present invention may have an asymmetric center and therefore may be optically active. The present invention includes not only racemic forms but also optically active forms.

Compounds of the general formula (1) can form an acid or base addition salt depending on the substituents. Therefore, the present invention includes pharmaceutically acceptable salts of the compounds of general formula (1). Examples of the acid addition salt of the compound of general formula (1) include inorganic acid salts such as hydrochloride, sulfate, nitrate and phosphate, as well as organic acid salts such as acetate, lactate, oxalate, citrate, tartrate and p-toluenesulfonate. Examples of the base addition salt of the compound of general formula (1) include inorganic base salts such as sodium, potassium, calcium, aluminum and ammonium salts, as well as organic amine salts.

Suitable compounds for the purpose of the present invention are as follows:

4,6-di-t-butyl-5-hydroxy-2,3-dihydrobenzofuran;
4,6-di-t-butyl-5-hydroxy-2-methyl-2,3-dihydrobenzofuran;
4,6-di-t-butyl-5-hydroxy-2,2-dimethyl-2,3-dihydrobenzofuran;
4,6-di-t-butyl-2,2-diethyl-5-hydroxy-2,3-dihydrobenzofuran;
4,6-di-t-butyl-2,2-di-n-propyl-5-hydroxy-2,3-dihydrobenzofuran;
4,6-di-t-butyl-2,2-di-n-butyl-5-hydroxy-2,3-dihydrobenzofuran;
4,6-di-t-butyl-5-hydroxy-2-n-octylbenzofuran;
4,6-di-t-butyl-5-hydroxy-2-n-octyl-2,3-dihydrobenzofuran;
2,4,6-tri-t-butyl-5-hydroxy-2,3-dihydrobenzofuran;
4,6-di-t-butyl-2,2-di-i-propyl-5-hydroxy-2,3-dihydrobenzofuran;
4,6-di-t-butyl-2,2-diphenyl-5-hydroxy-2,3-dihydrobenzofuran;
4,6-di-t-butyl-2,2-dibenzyl-5-hydroxy-2,3-dihydrobenzofuran;
4,6-di-t-butyl-2-chloromethyl-5-hydroxy-2,3-dihydrobenzofuran;
4,6-di-t-butyl-5-hydroxy-2,3-dihydrobenzofuran-2-spiro-1'-cyclopentane;
4,6-di-t-butyl-5-hydroxy-2,3-dihydrobenzofuran-2-spiro-1'-cyclohexane;
4,6-di-t-butyl-5-hydroxy-2,3-dihydrobenzofuran-2-spiro-1'-cycloheptane;
4,6-di-t-butyl-5-hydroxy-2,3-dihydrobenzofuran-2-spiro-1'-cyclooctane;
4,6-di-t-butyl-5-hydroxy-2,3-dihydrobenzofuran-2-spiro-4'-tetrahydropyran;
5-hydroxy-4,6-di-t-butyl-2,2-dimethyl-7-propyl-2,3-dihydrobenzofuran;
4,6-di-t-butyl-5-hydroxybenzofuran;
4,6-di-t-butyl-5-hydroxy-2-methylbenzofuran;
2,4,6-tri-t-butyl-5-hydroxybenzofuran;
2,6-di-t-butyl-3-methyl-4-propyloxyphenol;
4-allyloxy-2,6-di-t-butyl-3-methylphenol;
1,3-bis(3,5-di-t-butyl-4-hydroxy-2-methylphenoxy) propane;
4,6-di-t-butyl-2,2-di-n-pentyl-5-hydroxy-2,3-dihydrobenzofuran;
4,6-di-t-butyl-2,2-di-n-octyl-5-hydroxy-2,3-dihydrobenzofuran;
4,6-di-t-butyl-2,2-di-n-heptyl-5-hydroxy-2,3-dihydrobenzofuran;
4,6-di-t-butyl-2,2-di-n-hexyl-5-hydroxy-2,3-dihydrobenzofuran;
2,2-di-i-amyl-4,6-di-t-butyl-5-hydroxy-2,3-dihydrobenzofuran;
4,6-di-t-butyl-5-hydroxy-2-methyl-2-(4,8,12-trimethyltrideca-3(E),7(E),11-trienyl)-2,3-dihydrobenzofuran;
4,6-di-t-butyl-5-hydroxy-2-methyl-2-(4',8',12'-trimethyltridecyl)-2,3-dihydrobenzofuran;
4,6-di-t-butyl-5-hydroxy-2-(5-hydroxy-4-methyl-3(E)-pentenyl)-2-methyl-2,3-dihydrobenzofuran;
4,6-di-t-butyl-5-hydroxy-2-hydroxymethyl-2-methyl-2,3-dihydrobenzofuran;
4,6-di-t-butyl-5-hydroxy-2,2-di-n-pentyl-2,3-dihydrobenzothiophene;
4,6-di-t-butyl-5-hydroxy-2-methyl-2,3-dihydrobenzothiophene;
4,6-di-t-butyl-5-hydroxy-2,2-dimethyl-2,3-dihydrobenzothiophene;
4,6-di-t-butyl-5-hydroxybenzo[b]thiophene;
4,6-di-t-butyl-5-hydroxy-2,3-dihydrobenzothiophene;
4,6-di-t-butyl-5-hydroxy-2,2-diethyl-2,3-dihydrobenzothiophene;
4,6-di-t-butyl-5-hydroxy-2,2-di-n-propyl-2,3-dihydrobenzothiophene;
4,6-di-t-butyl-5-hydroxy-2,2-di-i-propyl-2,3-dihydrobenzothiophene;
4,6-di-t-butyl-5-hydroxy-2,2-di-n-butyl-2,3-dihydrobenzothiophene;
4,6-di-t-butyl-5-hydroxy-2,2-di-i-amyl-2,3-dihydrobenzothiophene;
4,6-di-t-butyl-5-hydroxy-2,2-di-n-hexyl-2,3-dihydrobenzothiophene;
4,6-di-t-butyl-5-hydroxy-2,2-di-n-heptyl-2,3-dihydrobenzothiophene;
4,6-di-t-butyl-5-hydroxy-2,2-di-n-octyl-2,3-dihydrobenzothiophene;
4,6-di-t-butyl-5-hydroxy-2,2-diphenyl-2,3-dihydrobenzothiophene;
4,6-di-t-butyl-5-hydroxy-2,2-dibenzyl-2,3-dihydrobenzothiophene;
4,6-di-t-butyl-5-hydroxy-2-methyl-2-(4,8,12-trimethyltrideca-3(E),7(E),11-trienyl)-2,3-dihydrobenzothiophene;
4,6-di-t-butyl-5-hydroxy-2-methyl-2-(4,8,12-trimethyltridecyl)-2,3-dihydrobenzothiophene;
4,6-di-t-butyl-5-hydroxy-2-n-octyl-2,3-dihydrobenzothiophene;
2,4,6-tri-t-butyl-5-hydroxy-2,3-dihydrobenzothiophene;
4,6-di-t-butyl-5-hydroxy-2,2-dimethyl-7-n-propyl-2,3-dihydrobenzothiophene;
4,6-di-t-butyl-5-hydroxy-2,3-dihydrobenzothiophene-2-spiro-1'-cyclopentane;
4,6-di-t-butyl-5-hydroxy-2,3-dihydrobenzothiophene-2-spiro-1'-cyclohexane;
4,6-di-t-butyl-5-hydroxy-2,3-dihydrobenzothiophene-2-spiro-1'-cycloheptane;
4,6-di-t-butyl-5-hydroxy-2,3-dihydrobenzothiophene-2-spiro-1-cyclooctane;
4,6-di-t-butyl-2-methyl-5-hydroxybenzo[b]thiophene;
2,4,6-tri-t-butyl-5-hydroxybenzo[b]thiophene;
4,6-di-t-butyl-2-n-octyl-5-hydroxybenzo[b]thiophene;
4,6-di-t-butyl-5-hydroxy-2-(N,N-dimethylaminomethyl)-2-methyl-2,3-dihydrobenzothiophene;
4,6-di-t-butyl-5-hydroxy-2-hydroxymethyl-2-methyl-2,3-dihydrobenzothiophene;

4,6-di-t-butyl-5-hydroxy-2-methyl-2-(4,8-dimethylnona-3(E),7-dienyl)-2,3-dihydrobenzothiophene;

4,6-di-t-butyl-5-hydroxy-2-methyl-2-(4,8-dimethylnonyl)-2,3-dihydrobenzothiophene;

4,6-di-t-butyl-5-hydroxy-2,3-dihydrobenzofuran-2-spiro-4'-tetrahydrothiopyran;

4,6-di-t-butyl-5-hydroxy-2,3-dihydrobenzothiophene-2-spiro-4'-tetrahydropyran;

2-aminomethyl-4,6-di-t-butyl-5-hydroxy-2-methyl-2,3-dihydrobenzofuran;

4,6-di-t-butyl-2-cyanomethyl-5-hydroxy-2-methyl-2,3-dihydrobenzofuran;

4,6-di-t-butyl-5-hydroxy-2-methyl-2,3-dihydrobenzofuran-2-carboxylic acid;

4,6-di-t-butyl-5-hydroxy-2-methoxycarbonyl-2-methyl-2,3-dihydrobenzofuran;

1-(4,6-di-t-butyl-5-hydroxy-2-methyl-2,3-dihydrobenzofuran-2-carbonyl)pyrrolidine;

Ethyl 3-(4,6-di-t-butyl-5-hydroxy-2-methyl-2,3-dihydrobenzofuran-2-yl)-2-propenoate;

Ethyl 3-(4,6-di-t-butyl-5-hydroxy-2-methyl-2,3-dihydrobenzofuran-2-yl)propanoate;

6-(4,6-di-t-butyl-5-hydroxy-2-methyl-2,3-dihydrobenzofuran-2-yl)-5-hexenoic acid;

6-(4,6-di-t-butyl-5-hydroxy-2-methyl-2,3-dihydrobenzofuran-2-yl)hexanoic acid;

4,6-di-t-butyl-5-hydroxy-2,3-dihydrobenzofuran-2-spiro-4'-(1'-methylpiperidine);

1-[(4,6-di-t-butyl-5-hydroxy-2-methyl-2,3-dihydrobenzofuran-2-yl)methyl]thiourea;

1-amino-3-[(4,6-di-t-butyl-5-hydroxy-2-methyl-2,3-dihydrobenzofuran-2-yl)methyl]guanidine;

4,6-di-t-butyl-5-hydroxy-2-methyl-2-(4-nitrophenoxymethyl)-2,3-dihydrobenzofuran;

2-(4-aminophenoxymethyl)-4,6-di-t-butyl-5-hydroxy-2-methyl-2,3-dihydrobenzofuran;

1-{4-[(4,6-di-t-butyl-5-hydroxy-2-methyl-2,3-dihydrobenzofuran-2-yl)methoxy]phenyl}guanidine;

1-{4-[(4,6-di-t-butyl-5-hydroxy-2-methyl-2,3-dihydrobenzofuran-2-yl)methoxy]benzylideneamino}guanidine;

1-{4-[(4,6-di-t-butyl-5-hydroxy-2-methyl-2,3-dihydrobenzofuran-2-yl)methoxy]benzylamino}guanidine; and 1-[(4,6-di-t-butyl-5-hydroxy-2-methyl-2,3-dihydrobenzofuran-2-yl)methylamino]guanidine.

Some compounds represented by the general formula (1) used in the present invention can be synthesized according to the procedures described in JP 6-206842/94 and 7-330759/95, for example.

Some compounds of the present invention can be synthesized according to the following schemes.

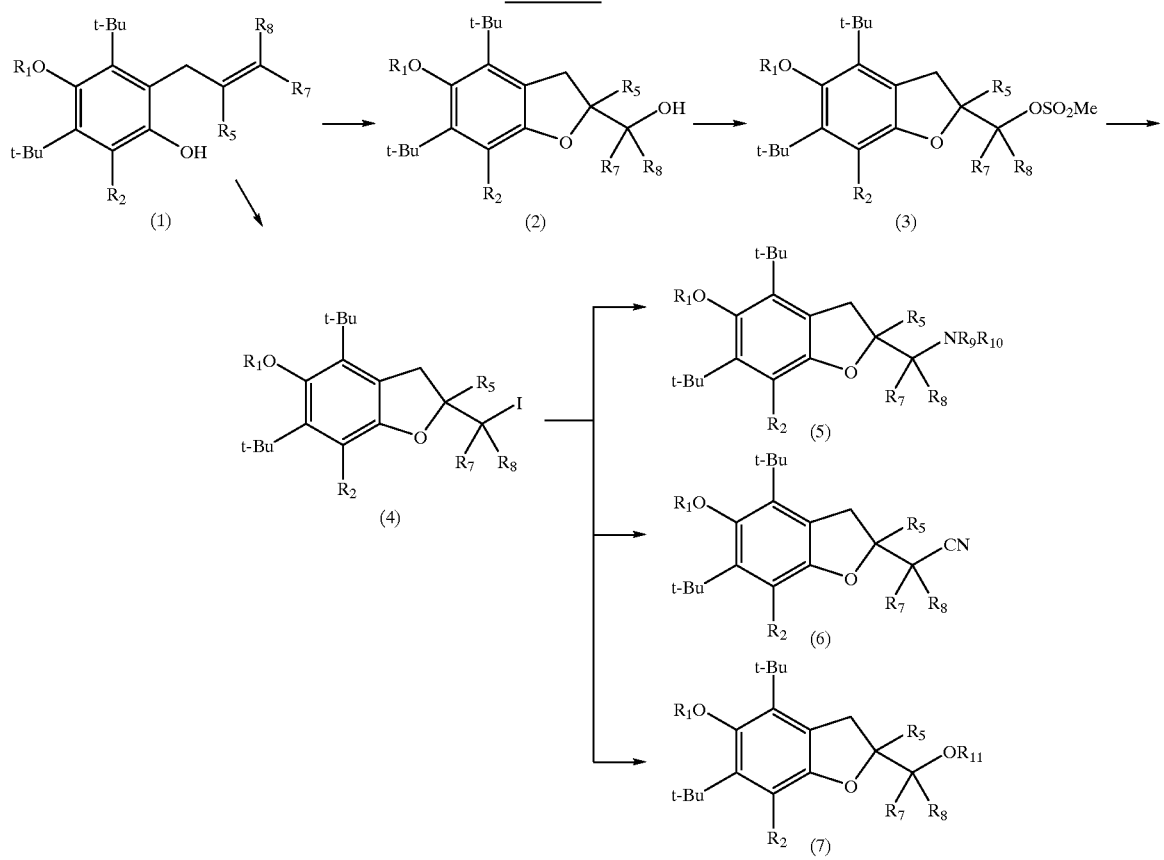

wherein $R_1$ represents a hydrogen atom or an acyl group, $R_2$ represents a hydrogen atom, a lower alkyl group or a lower alkenyl group, $R_5$, $R_7$ and $R_8$, which may be the same or different, each represents a hydrogen atom, an optionally substituted alkyl group or an optionally substituted alkenyl group, $R_9$ and $R_{10}$, which may be the same or different, each represents a hydrogen atom, a lower alkyl group or a lower alkenyl group, or $R_9$ and $R_{10}$ may be taken together to form a five- to eight-membered heterocyclic ring containing at least one nitrogen atom which may further contain one or more heteroatoms such as oxygen and sulfur atoms, and $R_{11}$ represents a hydrogen atom, an acyl group, a lower alkyl group, a lower alkenyl group or an optionally substituted aryl group.

(Scheme B)

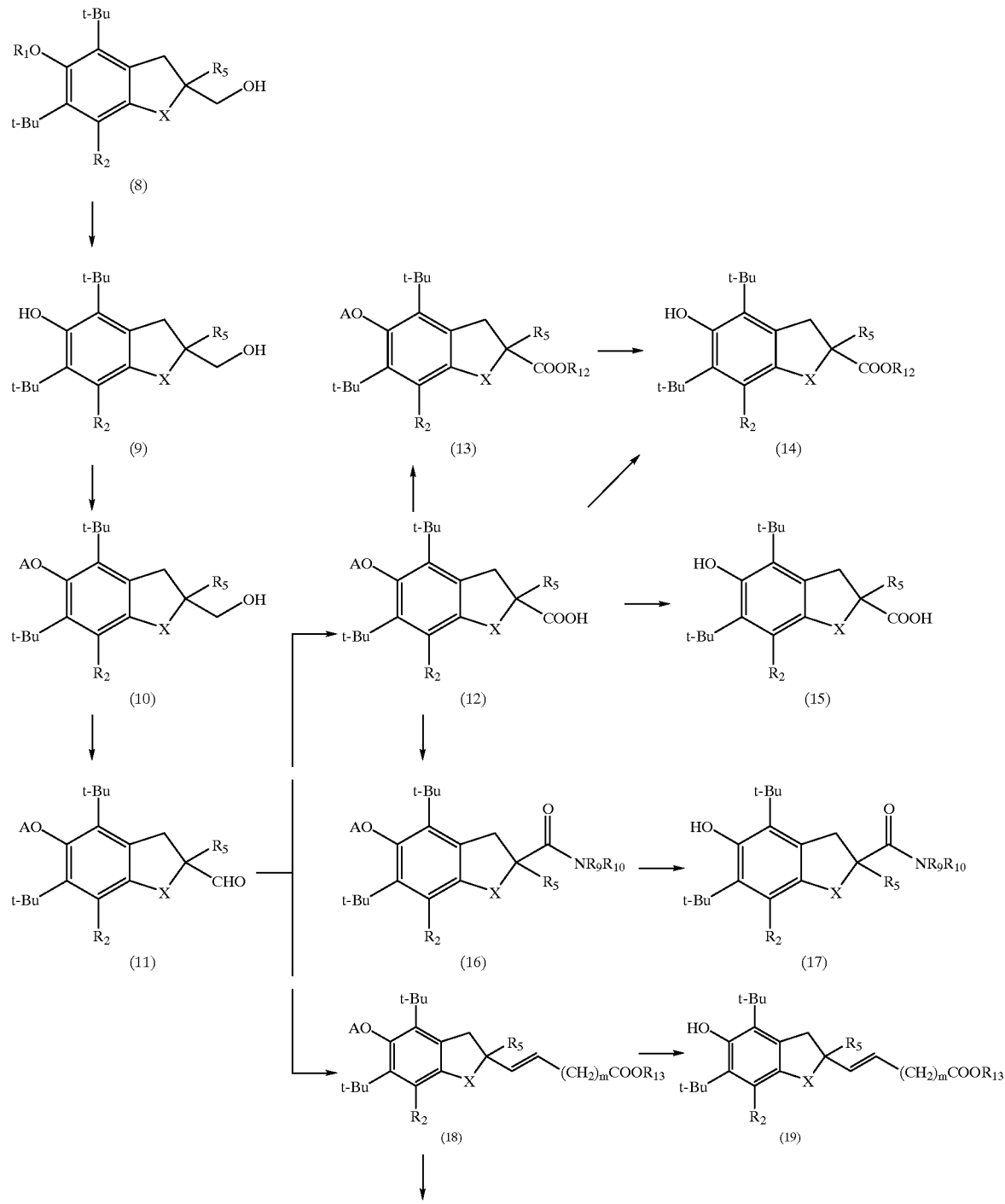

-continued

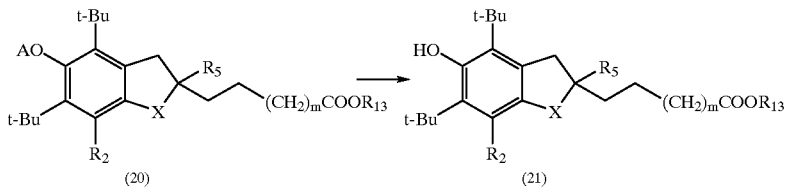

(20) → (21)

wherein $R_1$, $R_2$, $R_5$, $R_9$ and $R_{10}$ have the same meanings as defined above, A represents a protecting group such as trimethylsilyl, X represents an oxygen atom or a sulfur atom, $R_{12}$ represents an optionally substituted alkyl group, an optionally substituted alkenyl group, an optionally substituted alkynyl group or an optionally substituted aryl group, $R_{13}$ represents a hydrogen atom, an optionally substituted alkyl group, an optionally substituted alkenyl group, an optionally substituted alkynyl group or an optionally substituted aryl group, and m represents an integer of 0 to 18.

In Scheme A, the reaction for affording the compound of formula (4) is carried out by reacting the compound of formula (1), which is obtained according to the method described in JP 7-330759/95, in a mixed solvent of diethyl ether or the like and water in the presence of iodine and a base such as sodium bicarbonate at room temperature. Alternatively, the compound of formula (4) may be obtained by reacting the compound of formula (1) with m-chloroperbenzoic acid in a solvent such as chloroform, then with methanesulfonyl chloride in a solvent such as dichloromethane in the presence of a base such as triethylamine to give the compound of formula (3), which is then reacted with sodium iodide in a solvent such as N,N-dimethylformamide.

Various derivatives can be obtained from the compound of formula (4) according to the following three methods:

1. React the compound of formula (4) with ammonia or an alkyl amine such as a primary amine or a secondary amine in a solvent such as N,N-dimethylformamide in the presence of a base such as potassium carbonate at room temperature or with potassium phthalimide to give the compound of formula (5);
2. React the compound of formula (4) with potassium cyanide or the like in a solvent such as N,N-dimethylformamide or dimethyl sulfoxide to give a compound of formula (6); and
3. React the compound of formula (4) with an alkali metal carboxylate such as sodium acetate in a solvent such as N,N-dimethylformamide, dimethyl sulfoxide or hexamethylphosphoric triamide or with an alkyl alcohol or phenol in the presence of a base such as sodium hydride to give the compound of formula (7).

In Scheme B, the compound of formula (9) can be obtained by reacting compound (8) obtained either in said Scheme A or by the method described in JP 7-330759/95 with lithium aluminum hydride or diisobutylaluminum hydride in a solvent such as tetrahydrofuran or hexane. The compound of formula (10) can be obtained by reacting the compound of formula (9) with trimethylsilyl trifluoromethanesulfonate in the presence of a base such as 2,6-lutidine. The compound of formula (11) can be obtained by oxidizing the compound of formula (10) with a combination of dimethyl sulfoxide, oxalyl chloride and the like. Various derivatives can be obtained from the compound of formula (11) according to the following five methods:

1. Oxidize the compound of formula (11) with sodium chlorite in a mixture of t-butyl alcohol or the like and an aqueous sodium dihydrogenphosphate solution to give the compound of formula (12), which is then deprotected with tetra-n-butylammonium fluoride or the like in a solvent such as tetrahydrofuran to give the compound of formula (15);
2. React the compound of formula (12) with a catalytic amount of hydrogen chloride in an alkyl alcohol to give the compound of formula (14). Alternatively, react the compound (12) with an alkyl halide in a solvent such as N,N-dimethylformamide, dimethyl sulfoxide or hexamethylphosphoric triamide in the presence of a base such as sodium hydride to give the compound of formula (13), which is then deprotected with tetra-n-butylammonium fluoride or the like in a solvent such as tetrahydrofuran to give the compound of formula (14);
3. React the compound of formula (12) with an alkyl amine such as a primary amine or a secondary amine in a solvent such as dichloromethane in the presence of a condensing agent such as benzotriazole-1-yloxytris(dimethylamino)phosphonium hexafluorophosphate at room temperature to give the compound of formula (16), which is then deprotected with tetra-n-butylammonium fluoride or the like in a solvent such as tetrahydrofuran to give the compound of formula (17);
4. React the compound of formula (11) with a Wittig reagent or a Hornner-Emons reagent in a solvent such as tetrahydrofuran to give the compound of formula (18), which is then deprotected with tetra-n-butylammonium fluoride or the like in a solvent such as tetrahydrofuran to give the compound of formula (19); and
5. Subject the compound of formula (18) to a catalytic reduction in a solvent such as ethyl acetate in the presence of a transition metal catalyst such as palladium to give the compound of formula (20), which is then deprotected with tetra-n-butylammonium fluoride or the like in a solvent such as tetrahydrofuran to give the compound of formula (21).

Therapeutic agents for renal diseases of the present invention can be used as various pharmaceutical compositions comprising the compound of the general formula (1) as an active ingredient in combination with a physiologically innocuous solid or liquid pharmaceutical carrier. These pharmaceutical compositions are formulated and used in various dosage forms depending on the administration route. Dosage forms include tablets, granules, pills, capsules, solutions, syrups, suspensions, emulsions and injections. Suitable pharmaceutical carriers include commonly used excipients, binders, disintegrants, lubricants, coating agents, dissolution-aids, emulsifiers, suspending agents, stabilizers and solvents. The amount of an active ingredient represented by the general formula (1) contained in the pharmaceutical compositions of the present invention is generally 0.01–99% by weight, preferably 0.1–90% by weight.

The compound represented by the general formula (1) or the pharmaceutical composition described above of the present invention can be used via oral administration, parenteral administration such as intravenous injection, sustained administration with sustained-release formulations, etc.

Actually required amount of the compound represented by the general formula (1) for treating various renal diseases such as chronic renal failure, diabetic nephropathy, glomerular nephritis, immunocomplex nephritis, acute renal failure, nephropathies caused by platinum complex-based anticancer agents such as cisplatin or other drugs such as gentamicin, nephropathies caused by agrichemicals such as Paracort, uremia, etc. or for preserving an organ will vary depending on the age of the patient, the severity of condition, administration route or other factors. However, the amount will be 1–1000 mg, preferably 10–500 mg per day. It is preferable to administer such an amount in 1–3 doses to a patient in need of such treatment.

Organ preservatives of the present invention are used for any organ of humans and animals, such as brain, heart, kidney, pancreas, lung, liver and bone marrow cells. Kidney is a more preferable organ. The compound of the present invention can be added in a maintenance solution or a perfusion solution for an organ to minimize the damage of the organ during storage of the organ extracted from a donor for transplantation. Organ preservatives of the present invention can also inhibit deterioration of an extracted organ and thus can serve to maintain functions of the organs after transplantation.

For use as a preservative for maintaining organs, a normally acceptable effective amount of the compound represented by the general formula (1) is, for example, 1–1000 mg, which is used for a maintenance solution at a concentration of, for example, 0.1–10000 mg/L.

The following examples and test examples 1–4 further illustrate the present invention, but are not construed as limiting the same.

EXAMPLES

According to the procedure described in JP 6-206842/94, the following compounds of Examples 1–46 were synthesized.

Example 1
4,6-Di-t-butyl-5-hydroxy-2,3-dihydrobenzofuran

Example 2
4,6-Di-t-butyl-5-hydroxy-2-methyl-2,3-dihydrobenzofuran

Example 3
5-Acetoxy-4,6-di-t-butyl-2,2-dimethyl-2,3-dihydrobenzofuran

Example 4
4,6-Di-t-butyl-5-hydroxy-2,2-dimethyl-2,3-dihydrobenzofuran

Example 5
5-Acetoxy-4,6-di-t-butyl-2,2-diethyl-2,3-dihydrobenzofuran

Example 6
4,6-Di-t-butyl-2,2-diethyl-5-hydroxy-2,3-dihydrobenzofuran

Example 7
4,6-Di-t-butyl-2,2-di-n-propyl-5-hydroxy-2,3-dihydrobenzofuran

Example 8
4,6-Di-t-butyl-2,2-di-n-butyl-5-hydroxy-2,3-dihydrobenzofuran

Example 9
5-Acetoxy-4,6-di-t-butyl-2-(1-octenyl)benzofuran

Example 10
5-Acetoxy-4,6-di-t-butyl-2-n-octylbenzofuran

Example 11
4,6-Di-t-butyl-5-hydroxy-2-n-octylbenzofuran

Example 12
4,6-Di-t-butyl-5-hydroxy-2-n-octyl-2,3-dihydrobenzofuran

Example 13
2,4,6-Tri-t-butyl-5-hydroxy-2,3-dihydrobenzofuran

Example 14
4,6-Di-t-butyl-2,2-di-i-propyl-5-hydroxy-2,3-dihydrobenzofuran

Example 15
4,6-Di-t-butyl-2,2-diphenyl-5-hydroxy-2,3-dihydrobenzofuran

Example 16
4,6-Di-t-butyl-2,2-dibenzyl-5-hydroxy-2,3-dihydrobenzofuran

Example 17
4,6-Di-t-butyl-2-chloromethyl-5-hydroxy-2,3-dihydrobenzofuran

Example 18
4,6-Di-t-butyl-5-hydroxy-2,3-dihydrobenzofuran-2-spiro-1'-cyclopentane Example 19
4,6-Di-t-butyl-5-hydroxy-2,3-dihydrobenzofuran-2-spiro-1'-cyclohexane Example 20
4,6-Di-t-butyl-5-hydroxy-2,3-dihydrobenzofuran-2-spiro-1'-cycloheptane Example 21
4,6-Di-t-butyl-5-hydroxy-2,3-dihydrobenzofuran-2-spiro-1'-cyclooctane Example 22
4,6-Di-t-butyl-5-hydroxy-2,3-dihydrobenzofuran-2-spiro-4'-tetrahydropyran Example 23
4-Acetoxy-3,5-di-t-butyl-1-(2-methyl-2-propenyloxy)-2-propylbenzene Example 24
5-Acetoxy-4,6-di-t-butyl-2,2-dimethyl-7-propyl-2,3-dihydrobenzofuran Example 25
5-Hydroxy-4,6-di-t-butyl-2,2-dimethyl-7-propyl-2,3-dihydrobenzofuran Example 26
5-Acetoxy-4,6-di-t-butylbenzofuran Example 27
4,6-Di-t-butyl-5-hydroxybenzofuran Example 28
4,6-Di-t-butyl-5-hydroxy-2-methylbenzofuran

Example 29
2,4,6-Tri-t-butyl-5-hydroxybenzofuran

Example 30
1-Acetoxy-2,6-di-t-butyl-3-methyl-4-propyloxybenzene

Example 31
2,6-Di-t-butyl-3-methyl-4-propyloxyphenol

Example 32
1-Acetoxy-4-allyloxy-2,6-di-t-butyl-3-methylbenzene

Example 33
4-Allyloxy-2,6-di-t-butyl-3-methylphenol

Example 34
1,3-Bis(4-acetoxy-3,5-di-t-butyl-2-methylphenoxy)propane

Example 35
1,3-Bis(3,5-di-t-butyl-4-hydroxy-2-methylphenoxy)propane

Example 36
4,6-Di-t-butyl-2,2-di-n-pentyl-5-hydroxy-2,3-dihydrobenzofuran

Example 37
4,6-Di-t-butyl-2,2-di-n-octyl-5-hydroxy-2,3-dihydrobenzofuran

Example 38
4,6-Di-t-butyl-2,2-di-n-heptyl-5-hydroxy-2,3-dihydrobenzofuran

Example 39
4,6-Di-t-butyl-2,2-di-n-hexyl-5-hydroxy-2,3-dihydrobenzofuran

Example 40
5-Acetoxy-2,2-di-i-amyl-4,6-di-t-butyl-2,3-dihydrobenzofuran

Example 41
2,2-Di-i-amyl-4,6-di-t-butyl-5-hydroxy-2,3-dihydrobenzofuran

Example 42
5-Acetoxy-4,6-di-t-butyl-2-methyl-2-(4,8,12-trimethyltrideca-3(E),7(E),11-trienyl)-2,3-dihydrobenzofuran

Example 43
4,6-Di-t-butyl-5-hydroxy-2-methyl-2-(4,8,12-trimethyltrideca-3(E),7(E),11-trienyl)-2,3-dihydrobenzofuran

Example 44
4,6-Di-t-butyl-5-hydroxy-2-methyl-2-(4',8',12'-trimethyltridecyl)-2,3-dihydrobenzofuran

Example 45
5-Acetoxy-4,6-di-t-butyl-2-(5-hydroxy-4-methyl-3(E)-pentenyl)-2-methyl-2,3-dihydrobenzofuran

Example 46
4,6-Di-t-butyl-5-hydroxy-2-(5-hydroxy-4-methyl-3(E)-pentenyl)-2-methyl-2,3-dihydrobenzofuran

Example 47
5-Acetoxy-4,6-di-t-butyl-2-hydroxymethyl-2-methyl-2,3-dihydrobenzofuran In 200 ml of chloroform was dissolved 10.0 g of 4-acetoxy-3,5-di-t-butyl-2-(2-methyl-2-propenyl)phenol synthesized according to JP 7-330759/95 and 11.0 g of m-chloroperbenzoic acid was added, and the mixture was heated under reflux for 24 hours. After cooling, the reaction solution was combined with a saturated aqueous solution of sodium thiosulfate and extracted with chloroform. The organic layer was washed with saturated brine, dried over anhydrous magnesium sulfate, and then concentrated. The concentrate was purified by silica gel column chromatography eluting with n-hexane containing 25% ethyl acetate to give 7.3 g of 5-acetoxy-4,6-di-t-butyl-2-hydroxymethyl-2-methyl-2,3-dihydrobenzofuran (rotamer mixture) as a colorless oil (yield 70%).

$^1$H NMR (270 MHz, CDCl$_3$) δ ppm: 1.30 (s, 9H), 1.37 (s, 9H), 1.38 (s, 1.5H), 1.45 (s, 1.5H), 2.30 (s, 3H), 3.06 (d, 0.5H, J=15.5 Hz), 3.16 (d, 0.5H, J=15.5 Hz), 3.38 (d, 0.5H, J=15.5 Hz), 3.52 (d, 0.5H, J=15.5 Hz), 3.58–3.72 (m, 2H), 6.75 (s, 0.5H), 6.76 (s, 0.5H). Mass: 334 (M$^+$).

Example 48
4,6-Di-t-butyl-5-hydroxy-2-hydroxymethyl-2-methyl-2,3-dihydrobenzofuran Under a nitrogen atmosphere, a solution of 500 mg of 5-acetoxy-4,6-di-t-butyl-2-hydroxymethyl-2-methyl-2,3-dihydrobenzofuran in 7 ml of tetrahydrofuran was added dropwise to a suspension of 114 mg of lithium aluminum hydride in 3 ml of tetrahydrofuran. The mixture was heated under reflux for 2 hours and then cooled to room temperature. Ethyl acetate was added dropwise and then 10% hydrochloric acid was added, and the mixture was extracted with ethyl acetate. The organic layer was dried over anhydrous magnesium sulfate and then concentrated, and the concentrate was purified by silica gel column chromatography eluting with n-hexane containing 20% ethyl acetate to give 320 mg of 4,6-di-t-butyl-5-hydroxy-2-hydroxymethyl-2-methyl-2,3-dihydrobenzofuran as a white solid (yield 73%).

m.p.: 126–128° C. $^1$H NMR (270 MHz, CDCl$_3$) δ ppm: 1.38 (s, 3H), 1.40 (s, 9H), 1.49 (s, 9H), 2.04 (bs, 1H), 3.14 (d, 1H, J=15.5 Hz), 3.45 (d, 1H, J=15.5 Hz), 3.59 (d, 2H, J=1.65 Hz), 4.74 (s, 1H), 6.65 (s, 1H). IR (cm$^{-1}$): 3648, 3448, 2960. Mass: 292 (M$^+$).

According to the procedure described in JP 7-330759/95, the following compounds of Examples 49–67 were synthesized.

Example 49
5-Acetoxy-4,6-di-t-butyl-2,2-di-n-pentyl-2,3-dihydrobenzothiophene

Example 50
4,6-Di-t-butyl-5-hydroxy-2,2-di-n-pentyl-2,3-dihydrobenzothiophene

Example 51
4,6-Di-t-butyl-5-hydroxy-2-methyl-2,3-dihydrobenzothiophene

Example 52
4,6-Di-t-butyl-5-hydroxy-2,2-dimethyl-2,3-dihydrobenzothiophene

Example 53
5-Acetoxy-4,6-di-t-butylbenzo[b]thiophene

Example 54
4,6-Di-t-butyl-5-hydroxybenzo[b]thiophene

Example 55
5-Acetoxy-4,6-di-t-butylbenzo[b]thiophene-1,1-dioxide

Example 56
5-Acetoxy-4,6-di-t-butyl-2,3-dihydrobenzothiophene-1,1-dioxide

Example 57
4,6-Di-t-butyl-5-hydroxy-2,3-dihydrobenzothiophene

Example 58
4,6-Di-t-butyl-5-hydroxy-2,3-dihydrobenzothiophene-2-spiro-1'-cyclohexane

Example 59
5-Acetoxy-4,6-di-t-butyl-2-iodomethyl-2-methyl-2,3-dihydrobenzothiophene

Example 60
5-Acetoxy-4,6-di-t-butyl-2-(N,N-dimethylaminomethyl)-2-methyl-2,3-dihydrobenzothiophene

Example 61
4,6-Di-t-butyl-5-hydroxy-2-(N,N-dimethylaminomethyl)-2-methyl-2,3-dihydrobenzothiophene

Example 62
5-Acetoxy-2-acetoxymethyl-4,6-di-t-butyl-2-methyl-2,3-dihydrobenzothiophene

Example 63
4,6-Di-t-butyl-5-hydroxy-2-hydroxymethyl-2-methyl-2,3-dihydrobenzothiophene

Example 64
4,6-Di-t-butyl-5-hydroxy-2-methyl-2-(4,8-dimethylnona-3(E),7-dienyl)-2,3-dihydrobenzothiophene

Example 65
4,6-Di-t-butyl-5-hydroxy-2-methyl-2-(4,8-dimethylnonyl)-2,3-dihydrobenzothiophene

Example 66
4,6-Di-t-butyl-5-hydroxy-2-methyl-2-(4,8,12-trimethyltrideca-3(E),7(E),11-trienyl)-2,3-dihydrobenzothiophene

Example 67
4,6-Di-t-butyl-5-hydroxy-2-methyl-2-(4,8,12-trimethyltridecyl)-2,3-dihydrobenzothiophene

Example 68
4,6-Di-t-butyl-5-hydroxy-2,3-dihydrobenzofuran-2-spiro-4'-tetrahydrothiopyran 4,6-Di-t-butyl-5-hydroxy-2,3-dihydrobenzofuran-2-spiro-4'-tetrahydrothiopyran was synthesized according to the procedure described in JP 6-206842/94.

m.p.: 209.2° C. $^1$H NMR (270 MHz, CDCl$_3$) δ ppm: 1.41 (s, 9H), 1.48 (s, 9H), 1.77–1.94 (m, 2H), 2.09–2.21 (m, 2H), 2.45–2.58 (m, 2H), 2.98–3.12 (m, 2H), 3.18 (s, 2H), 4.73 (s, 1H), 6.66 (s, 1H). IR (cm$^{-1}$): 3628, 2936. Mass: 334 (M$^+$).

Example 69
4,6-Di-t-butyl-5-hydroxy-2,3-dihydrobenzothiophene-2-spiro-4'-tetrahydropyran 4,6-Di-t-butyl-5-hydroxy-2,3-dihydrobenzothiophene-2-spiro-4'-tetrahydropyran was synthesized according to the procedure described in JP 7-330759/95.

$^1$H NMR (270 MHz, CDCl$_3$) δ ppm: 1.40 (s, 9H), 1.53 (s, 9H), 1.87–1.92 (m, 4H), 3.38 (s, 2H), 3.61–3.70 (m, 2H), 3.86–3.91 (m, 2H), 5.15 (s, 1H), 6.98 (s, 1H). Mass: 334 (M$^+$).

Example 70
2-Aminomethyl-4,6-di-t-butyl-5-hydroxy-2-methyl-2,3-dihydrobenzofuran 1) Synthesis of 5-acetoxy-4,6-di-t-butyl-2-methanesulfonyloxymethyl-2-methyl-2,3-dihydrobenzofuran In 50 ml of dichloromethane was dissolved 0.5 g of 5-acetoxy-4,6-di-t-butyl-2-hydroxymethyl-2-methyl-2,3-dihydrobenzofuran synthesized in Example 47 and combined with 0.18 g of triethylamine and 0.2 g of methanesulfonyl chloride, and the mixture was stirred at room temperature for 24 hours. Then, the reaction mixture was combined with water and extracted with ethyl acetate, and the organic layer was washed with 10% hydrochloric acid and saturated brine, dried over anhydrous magnesium sulfate, and then concentrated. The concentrate was purified by silica gel column chromatography eluting with n-hexane containing 33% ethyl acetate to give 0.55 g of 5-acetoxy-4,6-di-t-butyl-2-methanesulfonyloxymethyl-2-methyl-2,3-dihydrobenzofuran (rotamer mixture) as a colorless oil (yield 89%).

$^1$H NMR (270 MHz, CDCl$_3$) δ ppm: 1.29 (s, 4.5H), 1.30 (s, 4.5H), 1.37 (s, 9H), 1.48 (s, 1.5H), 1.54 (s, 1.5H), 2.30 (s, 1.5H), 2.31 (s, 1.5H), 2.92 (s, 1.5H), 3.04 (s, 1.5H), 3.16 (d, 0.5H, J=15.8 Hz), 3.27 (d, 0.5H, J=15.8 Hz), 3.42 (d, 0.5H, J=15.8 Hz), 3.49 (d, 0.5H, J=15.8 Hz), 4.16–4.30 (m, 2H), 6.74 (s, 0.5H), 6.76 (s, 0.5H). Mass: 412 (M$^+$).

2) Synthesis of 5-acetoxy-4,6-di-t-butyl-2-iodomethyl-2-methyl-2,3-dihydrobenzofuran In 10 ml of N,N-dimethylformamide was dissolved 0.55 g of 5-acetoxy-4,6-di-t-butyl-2-methanesulfonyloxymethyl-2-methyl-2,3-dihydrobenzofuran and combined with 3.0 g of sodium iodide, and the mixture was heated under reflux for 24 hours. After cooling, water was added and the mixture was extracted with ethyl acetate, and the organic layer was washed with saturated brine, dried over anhydrous magnesium sulfate, and then concentrated. The concentrate was purified by silica gel column chromatography eluting with n-hexane containing 10% ethyl acetate to give 0.4 g of 5-acetoxy-4,6-di-t-butyl-2-iodomethyl-2-methyl-2,3-dihydrobenzofuran (rotamer mixture) as a colorless oil (yield 68%).

$^1$H NMR (270 MHz, CDCl$_3$) δ ppm: 1.30 (s, 9H), 1.38 (s, 9H), 1.61 (s, 1.5H), 1.67 (s, 1.5H), 2.30 (s, 3H), 3.22 (d, 0.5H, J=15.8 Hz), 3.34 (d, 0.5H, J=15.8 Hz), 3.40 (dd, 2H, J=16.5 Hz, J=13.5 Hz), 3.52 (d, 0.5H, J=15.8 Hz), 3.58 (d, 0.5H, J=15.8 Hz), 6.76 (s, 0.5H), 6.77 (s, 0.5H). Mass: 444 (M$^+$).

3) Alternative synthesis of 5-acetoxy-4,6-di-t-butyl-2-iodomethyl-2-methyl-2,3-dihydrobenzofuran In 200 ml of a mixed solvent of diethyl ether-water (3:1) was dissolved 10.0 g of 4-acetoxy-3,5-di-t-butyl-2-(2-methyl-2-propenyl)phenol synthesized according to the procedure described in JP 7-330759/95 and combined with 5.3 g of sodium bicarbonate and 12.0 g of iodine, and the mixture was stirred at room temperature for 20 minutes. Then, the reaction mixture was combined with a saturated aqueous sodium thiosulfate solution and extracted with ethyl acetate, and the organic layer was washed with saturated brine, dried over anhydrous magnesium sulfate, and then concentrated to give 13.2 g of 5-acetoxy-4,6-di-t-butyl-2-iodomethyl-2-methyl-2,3-dihydrobenzofuran (rotamer mixture) as a colorless oil (yield 95%).

4) Synthesis of 5-acetoxy-4,6-di-t-butyl-2-methyl-2-phthalimidemethyl-2,3-dihydrobenzofuran In 150 ml of dimethylformamide were suspended 14.2 g of 5-acetoxy-4,6-di-t-butyl-2-iodomethyl-2-methyl-2,3- dihydrobenzofuran and 7.0 g of potassium phthalimide, and the mixture was heated under stirring at 140° C. for 14 hours. After reaction, the mixture was cooled to room temperature, combined with a saturated aqueous ammonium chloride solution and extracted with ethyl acetate, and the organic layer was washed with saturated brine, dried over anhydrous magnesium sulfate, and then concentrated. The concentrate was purified by silica gel column chromatography eluting with n-hexane containing 20% ethyl acetate to give 13.4 g of 5-acetoxy-4,6-di-t-butyl-2-methyl-2-phthalimidemethyl-2,3-dihydrobenzofuran (rotamer mixture) as a white crystal (yield 92%).

$^1$H NMR (270 MHz, CDCl$_3$) δ ppm: 1.215 (s, 4.5H), 1.220 (s, 4.5H), 1.335 (s, 4.5H), 1.343 (s, 4.5H), 1.49 (s, 1.5H), 1.53 (s, 1.5H), 2.23 (s, 1.5H), 2.27 (s, 1.5H), 3.13–3.26 (m, 1H), 3.59–3.70 (m, 1H), 3.91–3.94 (m, 2H), 6.71 (s, 1H), 7.66–7.71 (m, 2H), 7.78–7.84 (m, 2H). Mass: 463 (M$^+$).

5) Synthesis of 5-acetoxy-2-aminomethyl-4,6-di-t-butyl-2-methyl-2,3-dihydrobenzofuran A suspension of 9.5 g of 5-acetoxy-4,6-di-t-butyl-2-methyl-2-phthalimidemethyl-2,3-dihydrobenzofuran in 150 ml of ethanol was combined with 1.24 g of hydrazine monohydrate at room temperature and the mixture was heated under reflux for 1 hour. After reaction, the mixture was cooled to room temperature and combined with 50 ml of 6N aqueous hydrochloric acid, and again heated under reflux for 30 minutes. After cooling to room temperature, the mixture was neutralized with a 2N aqueous sodium hydroxide solution and combined with chloroform to form insoluble matters. The mixture was filtered to remove the insoluble matters and the mother liquor was liquid-liquid partitioned. The organic layer was washed with saturated brine, dried over anhydrous magnesium sulfate, and then concentrated. The concentrate was purified by silica gel column chromatography eluting with chloroform containing 10% methanol to give 6.85 g of 5-acetoxy-2-aminomethyl-4,6-di-t-butyl-2-methyl-2,3-dihydrobenzofuran (rotamer mixture) as a colorless oil (quantitative).

$^1$H NMR (270 MHz, CDCl$_3$) δ ppm: 1.25 (s, 12H), 1.33 (s, 9H), 2.247 (s, 1.5H), 2.250 (s, 1.5H), 2.75–3.33 (m, 4H), 6.70 (s, 1H). Mass: 333 (M$^+$).

6) Synthesis of 2-aminomethyl-4,6-di-t-butyl-5-hydroxy-2-methyl-2,3-dihydrobenzofuran Under a nitrogen atmosphere, 13.2 ml of 1M diisobutyl aluminum hydride solution in toluene was added dropwise to a solution of 1.0 g of 5-acetoxy-2-aminomethyl-4,6-di-t-butyl-2-methyl-2,3-dihydrobenzofuran in 30 ml of toluene at room temperature. After stirring at room temperature for 14 hours, the mixture was combined with water and extracted with ethyl acetate, and the resulting organic layer was washed with saturated brine, dried over anhydrous magnesium sulfate, and then concentrated. The concentrate was purified by recrystallization from a mixed solvent of ethyl acetate and hexane to give 0.62 g of 2-aminomethyl-4,6-di-t-butyl-5-hydroxy-2-methyl-2,3-dihydrobenzofuran as a white crystal (yield 71%).

$^1$H NMR (270 MHz, CDCl$_3$) δ ppm: 1.40 (s, 3H), 1.43 (s, 9H), 1.52 (s, 9H), 2.83 (s, 2H), 3.17 (d, 1H, J=15.7 Hz), 3.37 (d, 1H, J=15.7 Hz), 4.74 (s, 1H), 6.67 (s, 1H). Mass: 291 (M$^+$).

Example 71

4,6-Di-t-butyl-2-cyanomethyl-5-hydroxy-2-methyl-2,3-dihydrobenzofuran

In 5 ml of dimethyl sulfoxide were dissolved 1.00 g of 5-acetoxy-4,6-di-t-butyl-2-iodomethyl-2-methyl-2,3-dihydrobenzofuran synthesized in Example 70-2) and 0.36 g of potassium cyanide and the mixture was heated with stirring at 140° C. under nitrogen overnight. After cooling to room temperature, the reaction solution was poured into water and extracted with ether, and the combined organic layers were washed with saturated brine, dried over anhydrous magnesium sulfate, and then concentrated. The residue was purified by silica gel column chromatography eluting with n-hexane containing 9–13% ethyl acetate to give 0.09 g of 4,6-di-t-butyl-2-cyanomethyl-5-hydroxy-2-methyl-2,3-dihydrobenzofuran as a colorless solid (yield 13%).

$^1$H NMR (270 MHz, CDCl$_3$) δ ppm: 1.40 (s, 9H), 1.49 (s, 9H), 1.61 (s, 3H), 2.68 (d, 2H, J=2.3 Hz), 3.32 (d, 1H, J=15.8 Hz), 3.44 (d, 1H, J=15.8 Hz), 4.80 (s, 1H), 6.67 (s, 1H). Mass: 301 (M$^+$).

Example 72

4,6-Di-t-butyl-5-hydroxy-2-methyl-2,3-dihydrobenzofuran-2-carboxylic acid

1) Synthesis of 4,6-di-t-butyl-2-hydroxymethyl-2-methyl-5-trimethylsilyloxy-2,3-dihydrobenzofuran A solution of 0.59 g of 4,6-di-t-butyl-5-hydroxy-2-hydroxymethyl-2-methyl-2,3-dihydrobenzofuran synthesized in Example 48 and 1.17 ml of 2,6-luthidine in 5 ml of dichloromethane was cooled to 0° C. under nitrogen, combined with 1.25 ml of trimethylsilyl trifluoromethanesulfonate and stirred. After 30 minutes, the reaction solution was poured into water and extracted with ether, and the combined organic layers were concentrated. The residue was dissolved in 10 ml of THF, 5% hydrochloric acid was added and the solution was stirred for 1 hour, after which the reaction solution was concentrated and extracted with water and ether. The combined organic layers were washed with a saturated aqueous sodium bicarbonate solution, dried over anhydrous magnesium sulfate and then concentrated. The residue was purified by silica gel column chromatography eluting with n-hexane containing 9% ethyl acetate to give 0.62 g of 4,6-di-t-butyl-2-hydroxymethyl-2-methyl-5-trimethylsilyloxy-2,3-dihydrobenzofuran as a colorless oil (yield 84%).

$^1$H NMR (270 MHz, CDCl$_3$) δ ppm: 0.30 (s, 9H), 1.38 (s, 12H), 1.45 (s, 9H), 3.07 (d, 1H, J=15.5 Hz), 3.41 (d, 1H, J=15.5 Hz), 3.58 (bs, 2H), 6.69 (s, 1H). Mass: 365 (M$^+$+1).

2) Synthesis of 4,6-di-t-butyl-2-formyl-2-methyl-5-trimethylsilyloxy-2,3-dihydrobenzofuran To a solution of 0.43 ml of dimethyl sulfoxide in 12 ml of dichloromethane cooled to −78° C. under nitrogen was added dropwise 0.26 ml of oxalyl chloride. After 15 minutes, a solution of 4,6-di-t-butyl-2-hydroxymethyl-2-methyl-5-trimethylsilyloxy-2,3-dihydrobenzofuran in 5 ml of dichloromethane was added dropwise. After further 15 minutes, 1.91 ml of triethylamine was added dropwise and then the mixture was slowly warmed to room temperature. After one hour, the reaction solution was poured into water and extracted with dichloromethane, and the combined organic layers were washed with saturated brine, dried over anhydrous magnesium sulfate, and then concentrated. The residue was purified on a short column of silica gel eluting with n-hexane containing 9% ethyl acetate to give 1.04 g of 4,6-di-t-butyl-2-formyl-2-methyl-5-trimethylsilyloxy-2,3-dihydrobenzofuran containing impurities.

$^1$H NMR (270 MHz, CDCl$_3$) δ ppm: 0.28 (s, 9H), 1.37 (s, 9H), 1.42 (s, 9H), 1.50 (s, 3H), 3.19 (d, 1H, J=15.5 Hz), 3.64 (d, 1H, J=15.5 Hz), 6.78 (s, 1H), 9.71 (s, 1H). Mass: 363 (M$^+$+1).

3) Synthesis of 4,6-di-t-butyl-2-methyl-5-trimethylsilyloxy-2,3-dihydrobenzofuran-2-carboxylic acid To a solution of 0.5 g of 4,6-di-t-butyl-2-formyl-2-methyl-5-trimethylsilyloxy-2,3-dihydrobenzofuran in 5 ml of t-butyl alcohol were added 5 ml of a saturated aqueous sodium dihydrogenphosphate solution and 0.73 ml of 2-methyl-2-butene, and the mixture was cooled to −5° C. To this solution was added dropwise a solution of 0.14 g of sodium chlorite in 5 ml of distilled water, and the mixture was stirred for 20 minutes, then further stirred at room temperature for 15 minutes. The reaction solution was extracted with diethyl ether, and the combined organic layers were washed with saturated brine, dried over anhydrous magnesium sulfate, and then concentrated. The residue was recrystallized from hexane to give 0.38 g of 4,6-di-t-butyl-2-methyl-5-trimethylsilyloxy-2,3-dihydrobenzofuran-2-carboxylic acid as a colorless powder (yield 73%).

$^1$H NMR (270 MHz, CDCl$_3$) δ ppm: 0.28 (s, 9H), 1.37 (s, 9H), 1.42 (s, 9H), 1.69 (s, 3H), 3.36 (d, 1H, J=15.8 Hz), 3.84 (d, 1H, J=15.8 Hz), 6.80 (s, 1H). Mass: 378 (M$^+$).

4) Synthesis of 4,6-di-t-butyl-5-hydroxy-2-methyl-2,3-dihydrobenzofuran-2-carboxylic acid Under a nitrogen atmosphere, a solution of 0.19 g of 4,6-di-t-butyl-2-methyl-5-trimethylsilyloxy-2,3-dihydrobenzofuran-2-carboxylic acid in 1 ml of THF was cooled to 0° C. and 1 ml of tetra-n-butylammonium fluoride (1.0 mmol/ml THF solution) was added dropwise to this solution and the mixture was stirred for 1 hour. After the reaction was quenched by adding a saturated aqueous ammonium chloride solution, the mixture was extracted with water and diethyl ether, and the combined organic layers were washed with saturated brine, dried over anhydrous magnesium sulfate, and then concentrated to give 0.14 g of 4,6-di-t-butyl-5-hydroxy-2-methyl-2,3-dihydrobenzofuran-2-carboxylic acid as a colorless solid (yield 91%).

$^1$H NMR (270 MHz, CDCl$_3$) δ ppm: 1.43 (s, 9H), 1.48 (s, 9H), 1.70 (s, 3H), 3.39 (d, 1H, J=16.2 Hz), 3.92 (d, 1H, J=16.2 Hz), 6.77 (s, 1H). Mass: 306 (M$^+$).

Example 73

4,6-Di-t-butyl-5-hydroxy-2-methoxycarbonyl-2-methyl-2,3-dihydrobenzofuran

In 5 ml of a saturated solution of hydrogen chloride in methanol was dissolved 0.20 g of 4,6-di-t-butyl-2-methyl-5-trimethylsilyloxy-2,3-dihydrobenzofuran-2-carboxylic acid at room temperature and the mixture was stirred for 3 hours, then the reaction solution was concentrated. The residue was purified on a short column of silica gel eluting with n-hexane containing 16% ethyl acetate to give 0.15 g of 4,6-di-t-butyl-5-hydroxy-2-methoxycarbonyl-2-methyl-2,3-dihydrobenzofuran as a colorless powder.

$^1$H NMR (270 MHz, CDCl$_3$) δ ppm: 1.41 (s, 9H), 1.49 (s, 9H), 1.66 (s, 3H), 3.36 (d, 1H, J=16.0 Hz), 3.78 (s, 3H), 3.91 (d, 1H, J=16.0 Hz), 4.79 (s, 1H), 6.78 (s, 1H). Mass: 321 (M$^+$+1).

Example 74

1-(4,6-Di-t-butyl-5-hydroxy-2-methyl-2,3-dihydrobenzofuran-2-carbonyl)pyrrolidine 1) Synthesis of 1-(4,6-di-t-butyl-2-methyl-5-trimethylsilyloxy-2,3-dihydrobenzofuran-2-carbonyl) pyrrolidine In 3 ml of dichloromethane were dissolved 0.20 g of 4,6-di-t-butyl-2-methyl-5-trimethylsilyloxy-2,3-dihydrobenzofuran-2-carboxylic acid, 0.20 ml of triethylamine and 0.06 ml of pyrrolidine at room temperature, and 0.35 g of benzotriazol-1-yloxytris(dimethylamino) phosphonium hexafluorophosphate was added and the mixture was stirred for 4 hours. The mixture was extracted with water and diethyl ether, and the combined organic layers were washed with saturated brine and dried over anhydrous magnesium sulfate. After concentration, the residue was purified by silica gel column chromatography eluting with n-hexane containing 33% ethyl acetate to give 0.21 g of 1-(4,6-di-t-butyl-2-methyl-5-trimethylsilyloxy-2,3-dihydrobenzofuran-2-carbonyl)pyrrolidine as a colorless solid (yield 92%).

$^1$H NMR (270 MHz, CDCl$_3$) δ ppm: 0.27 (s, 9H), 1.37 (s, 9H), 1.42 (s, 9H), 1.59 (s, 3H), 1.73–1.88 (m, 4H), 3.22 (d, 1H, J=15.8 Hz), 3.45–3.78 (m, 4H), 4.06 (d, 1H, J=15.8 Hz), 6.67 (s, 1H). Mass: 431 (M$^+$).

2) Synthesis of 1-(4,6-di-t-butyl-5-hydroxy-2-methyl-2,3-dihydrobenzofuran-2-carbonyl)pyrrolidine 1-(4,6-di-t-butyl-2-methyl-5-trimethylsilyloxy-2,3-dihydrobenzofuran-2-carbonyl)pyrrolidine was treated in the same manner as in Example 72-4) to give 0.11 g of 1-(4,6-di-t-butyl-5-hydroxy-2-methyl-2,3-dihydrobenzofuran-2-carbonyl)pyrrolidine as a colorless solid (yield 63%).

$^1$H NMR (270 MHz, CDCl$_3$) δ ppm: 1.41 (s, 9H), 1.49 (s, 9H), 1.62 (s, 3H), 1.74–2.04 (m, 4H), 3.27 (d, 1H, J=16.2 Hz), 3.45–3.69 (m, 4H), 4.21 (d, 1H, J=16.2 Hz), 4.82 (s, 1H), 6.66 (s, 1H). Mass: 359 (M$^+$).

Example 75

Ethyl 3-(4,6-di-t-butyl-5-hydroxy-2-methyl-2,3-dihydrobenzofuran-2-yl)-2-propenoate 1) Synthesis of ethyl 3-(4,6-di-t-butyl-2-methyl-5-trimethylsilyloxy-2,3-dihydrobenzofuran-2-yl)-2-propenoate Under nitrogen, a suspension of 0.17 g of sodium hydride in 12 ml of THF was cooled to 0° C. and 0.68 ml of triethyl phosphonoacetate was added dropwise. After stirring for 15 minutes, the solution was warmed to room temperature and cooled again to 0° C., and a solution of 4,6-di-t-butyl-2-formyl-2-methyl-5-trimethylsilyloxy-2,3-dihydrobenzofuran synthesized in Example 72-2) in 5 ml of THF was added dropwise. After 1 hour, the reaction solution was quenched by adding a saturated aqueous ammonium chloride solution. The reaction solution was extracted with water and diethyl ether, and the combined organic layers were washed with saturated brine, then dried over anhydrous magnesium sulfate and concentrated. The residue was purified by silica gel column chromatography eluting with n-hexane containing 1.5–2% ethyl acetate to give 0.54 g of ethyl 3-(4,6-di-t-butyl-2-methyl-5-trimethylsilyloxy-2,3-dihydrobenzofuran-2-yl)-2-propenoate as a colorless liquid (yield 91%).

$^1$H NMR (270 MHz, CDCl$_3$) δ ppm: 0.27 (s, 9H), 1.28 (t, 3H, J=7.3 Hz), 1.37 (s, 9H), 1.53 (s, 3H), 1.45 (s, 9H), 3.28 (d, 1H, J=15.3 Hz), 3.38 (d, 1H, J=15.3 Hz), 4.19 (q, 2H, J=7.3 Hz), 6.03 (d, 1H, J=15.3 Hz), 6.72 (s, 1H), 7.01 (d, 1H, 15.3 Hz). Mass: 433 (M$^+$+1).

2) Synthesis of ethyl 3-(4,6-di-t-butyl-5-hydroxy-2-methyl-2,3-dihydrobenzofuran-2-yl)-2-propenoate 0.14 g of ethyl 3-(4,6-di-t-butyl-2-methyl-5-trimethylsilyloxy-2,3-dihydrobenzofuran-2-yl)-2-propenoate was treated in the same manner as in Example 72-4) to give 0.09 g of ethyl 3-(4,6-di-t-butyl-5-hydroxy-2-methyl-2,3-dihydrobenzofuran-2-yl)-2-propenoate as a colorless viscous liquid (yield 77%).

$^1$H NMR (270 MHz, CDCl$_3$) δ ppm: 1.29 (t, 3H, J=6.8 Hz), 1.42 (s, 9H), 1.48 (s, 9H), 1.55 (s, 3H), 3.36 (d, 1H, J=15.7 Hz), 3.47 (d, 1H, J=15.7 Hz), 4.19 (q, 2H, J=6.8 Hz), 4.76 (s, 1H), 6.07 (d, 1H, J=15.8 Hz), 6.71 (s, 1H), 7.01 (d, 1H, J=15.8 Hz). Mass: 360 (M$^+$).

Example 76
Ethyl 3-(4,6-di-t-butyl-5-hydroxy-2-methyl-2,3-dihydrobenzofuran-2-yl)propanoate 1) Synthesis of ethyl 3-(4,6-di-t-butyl-2-methyl-5-trimethylsilyloxy-2,3-dihydrobenzofuran-2-yl)propanoate To a solution of 0.27 g of ethyl 3-(4,6-di-t-butyl-2-methyl-5-trimethylsilyloxy-2,3-dihydrobenzofuran-2-yl)-2-propenoate synthesized in Example 75-1) in 20 ml of ethanol was added a catalytic amount of 10% palladium-carbon, and the mixture was stirred for 48 hours under a hydrogen atmosphere. After the catalyst was filtered off, the filtrate was concentrated and the residue was purified on a short column of silica gel eluting with n-hexane containing 9% ethyl acetate to give 0.27 g of ethyl 3-(4,6-di-t-butyl-2-methyl-5-trimethylsilyloxy-2,3-dihydrobenzofuran-2-yl)propanoate as a colorless viscous liquid.

$^1$H NMR (270 MHz, CDCl$_3$) δ ppm: 0.28 (s, 9H), 1.24 (t, 3H, J=7.3 Hz), 1.36 (s, 9H), 1.37 (s, 3H), 1.42 (s, 9H), 1.97–2.04 (m, 2H), 2.38–2.44 (m, 2H), 3.13 (d, 1H, J=15.2 Hz), 3.22 (d, 1H, J=15.2 Hz), 4.12 (q, 2H, J=7.3 Hz), 6.63 (s, 1H). Mass: 434 (M$^+$).

2) Synthesis of ethyl 3-(4,6-di-t-butyl-5-hydroxy-2-methyl-2,3-dihydrobenzofuran-2-yl)propanoate 0.12 g of ethyl 3-(4,6-di-t-butyl-2-methyl-5-trimethylsilyloxy-2,3-dihydrobenzofuran-2-yl)propanoate was treated in the same manner as in Example 72-4) to give 0.09 g of ethyl 3-(4,6-di-t-butyl-5-hydroxy-2-methyl-2,3-dihydrobenzofuran-2-yl)propanoate as a colorless viscous liquid (yield 90%).

$^1$H NMR (270 MHz, CDCl$_3$) δ ppm: 1.24 (t, 3H, J=7.1 Hz), 1.38 (s, 3H), 1.40 (s, 9H), 1.48 (s, 9H), 1.94–2.05 (m, 2H), 2.46 (t, 2H, J=8.1 Hz), 3.19 (d, 1H, J=15.5 Hz), 3.28 (d, 1H, J=15.5 Hz), 4.12 (q, 2H, J=7.1 Hz), 4.70 (s, 1H), 6.61 (s, 1H). Mass: 362 (M$^+$).

Example 77
6-(4,6-Di-t-butyl-5-hydroxy-2-methyl-2,3-dihydrobenzofuran-2-yl)-5-hexenoic acid Under a nitrogen atmosphere, a solution of 0.92 g of potassium t-butoxide in 10 ml of THF was added dropwise to a suspension of 0.46 g of 5-carboxypentyltriphenylphosphonium bromide in 5 ml of THF at 0° C., and the mixture was stirred for 30 minutes. To the reaction solution was added dropwise a solution of 4,6-di-t-butyl-2-formyl-2-methyl-5-trimethylsilyloxy-2,3-dihydrobenzofuran synthesized in Example 72-2) in 10 ml of THF, and the mixture was stirred overnight while slowly warming to room temperature. The reaction solution was extracted with water and diethyl ether, and the combined aqueous layers were acidified with concentrated hydrochloric acid and extracted with diethyl ether. The organic layer was washed with saturated brine, dried over anhydrous magnesium sulfate and concentrated. The residue was purified by silica gel column chromatography eluting with n-hexane containing 50% ethyl acetate to give 0.22 g of 6-(4,6-di-t-butyl-5-hydroxy-2-methyl-2,3-dihydrobenzofuran-2-yl)-5-hexenoic acid as a colorless viscous liquid (yield 43%).

$^1$H NMR (270 MHz, CDCl$_3$) δ ppm: 0.99–1.39 (m, 2H), 1.41 (s, 9H), 1.48 (s, 9H), 1.49 (s, 3H), 1.61–1.77 (m, 4H), 3.36 (d, 1H, J=15.7 Hz), 3.44 (d, 1H, J=15.7 Hz), 4.71 (s, 1H), 5.31–5.38 (m, 1H), 5.66 (d, 1H, J=11.9 Hz), 6.65 (s, 1H). Mass: 374 (M$^+$).

Example 78
6-(4,6-Di-t-butyl-5-hydroxy-2-methyl-2,3-dihydrobenzofuran-2-yl)hexanoic acid To a solution of 0.11 g of 6-(4,6-di-t-butyl-5-hydroxy-2-methyl-2,3-dihydrobenzofuran-2-yl)-5-hexenoic acid synthesized in Example 77 in 10 ml of ethyl acetate was added a catalytic amount of 10% palladium-carbon, and the mixture was stirred for 24 hours under a hydrogen atmosphere. After the catalyst was filtered off, the filtrate was concentrated to give 0.10 g of 6-(4,6-di-t-butyl-5-hydroxy-2-methyl-2,3-dihydrobenzofuran-2-yl)hexanoic acid as a colorless viscous liquid (yield 90%).

$^1$H NMR (270 MHz, CDCl$_3$) δ ppm: 1.00–1.48 (m, 6H), 1.35 (s, 3H), 1.40 (s, 9H), 1.49 (s, 9H), 1.61–1.68 (m, 2H), 2.35 (t, 2H, J=7.3 Hz), 3.15 (d, 1H, J=15.5 Hz), 3.26 (d, 1H, J=15.5 Hz), 4.69 (s, 1H), 6.62 (s, 1H). Mass: 376 (M$^+$).

Example 79
4,6-Di-t-butyl-5-hydroxy-2,3-dihydrobenzofuran-2-spiro-4'-(1'-methylpiperidine)

4,6-Di-t-butyl-5-hydroxy-2,3-dihydrobenzofuran-2-spiro-4'-(1'-methylpiperidine) was synthesized according to the procedure described in JP 6-206842/94.

$^1$H NMR (270 MHz, CDCl$_3$) δ ppm: 1.41 (s, 9H), 1.49 (s, 9H), 1.72–1.80 (m, 2H), 1.82–1.96 (m, 2H), 2.34 (s, 3H), 2.55 (br, 4H), 3.20 (s, 2H), 4.71 (s, 1H), 6.66 (s, 1H). IR (cm$^{-1}$): 3650, 2944. Mass: 331 (M$^+$).

Example 80
1-[(4,6-Di-t-butyl-5-hydroxy-2-methyl-2,3-dihydrobenzofuran-2-yl)methyl]thiourea 1) Synthesis of (5-acetoxy-4,6-di-t-butyl-2-methyl-2,3-dihydrobenzofuran-2-yl)methyl isothiocyanate To an ice-cooled suspension of 4.56 g of dicyclohexylcarbodiimide and 8 ml of carbon disulfide in 20 ml of tetrahydrofuran was added dropwise a solution of 6.18 g of 5-acetoxy-2-aminomethyl-4,6-di-t-butyl-2-methyl-2,3-dihydrobenzofuran synthesized in Example 70-5) in 20 ml of tetrahydrofuran. The mixture was stirred at 0° C. for 2 hours and then stirred at room temperature for 24 hours. After reaction, carbon disulfide and tetrahydrofuran were removed using an evaporator and the precipitated dicyclohexylthiourea was filtered off. Then, water was added to the filtrate and the solution was extracted with ethyl acetate. The organic layer was washed with saturated brine, dried over anhydrous magnesium sulfate, and then concentrated. The concentrate was purified by silica gel column chromatography eluting with n-hexane containing 10% ethyl acetate to give 5.15 g of (5-acetoxy-4,6-di-t-butyl-2-methyl-2,3-dihydrobenzofuran-2-yl)methyl isothiocyanate (rotamer mixture) as a colorless oil (yield 74%).

$^1$H NMR (270 MHz, CDCl$_3$) δ ppm: 1.30 (s, 9H), 1.37 (s, 4.5H), 1.38 (s, 4.5H), 1.49 (s, 1.5H), 1.59 (s, 1.5H), 2.30 (s, 3H), 3.20 (d, 0.5H, J=15.8 Hz), 3.28 (s, 0.5H), 3.43 (d, 0.5H, J=15.8 Hz), 3.54 (d, 0.5H, J=14.2 Hz), 3.646 (s, 1H), 3.654 (s, 1H), 6.767 (s, 0.5H), 6.774 (s, 0.5H). Mass: 375 (M$^+$).

2) Synthesis of 1-[(5-acetoxy-4,6-di-t-butyl-2-methyl-2,3-dihydrobenzofuran-2-yl)methyl]thiourea To a solution of 4.16 g of a 28% aqueous ammonia solution in 10 ml of ethanol was added dropwise a solution of 5.15 g of (5-acetoxy-4,6-di-t-butyl-2-methyl-2,3-dihydrobenzofuran-2-yl)methyl isothiocyanate in 20 ml of ethanol at room temperature. The mixture was stirred at room temperature for 2 hours, and then heated under reflux for further 1 hour. After cooling, ethanol was removed using an evaporator, and the mixture was combined with water and extracted with chloroform. The organic layer was washed with saturated brine, dried over anhydrous magnesium sulfate, and then concentrated. The concentrate was purified by silica gel column chromatography eluting with chloroform containing 10% methanol to give 5.3 g of 1-[(5-acetoxy-4,6-di-t-butyl-2-methyl-2,3-dihydrobenzofuran-2-yl)methyl]thiourea (rotamer mixture) as a white solid (yield 99%).

¹H NMR (270 MHz, CDCl₃) δ ppm: 1.27 (s, 4.5H), 1.29 (s, 4.5H), 1.34 (s, 4.5H), 1.35 (s, 4.5H), 1.38 (s, 1.5H), 1.46 (s, 1.5H), 2.29 (s, 1.5H), 2.30 (s, 1.5H), 3.10 (d, 0.5H, J=15.8 Hz), 3.18 (d, 0.5H, J=16.2 Hz), 3.39 (d, 0.5H, J=15.8 Hz), 3.56–3.65 (m, 0.5H), 3.70–4.05 (m, 2H), 6.71 (s, 0.5H), 6.74 (s, 0.5H). Mass: 392 (M⁺).

3) Synthesis of 1-[(4,6-di-t-butyl-5-hydroxy-2-methyl-2,3-dihydrobenzofuran-2-yl)methyl]thiourea Under a nitrogen atmosphere, 1.0 g of 1-[(5-acetoxy-4,6-di-t-butyl-2-methyl-2,3-dihydrobenzofuran-2-yl)methyl]thiourea was dissolved in 30 ml of toluene. To the solution was added 10.2 ml of diisobutyl aluminum hydride (1.0 M in toluene) and the mixture was stirred at room temperature for 1 hour. After reaction, the mixture was combined with a saturated aqueous ammonium chloride solution and 10% hydrochloric acid and extracted with ethyl acetate. The organic layer was washed with saturated brine, dried over anhydrous magnesium sulfate, and then concentrated. The concentrate was purified by silica gel column chromatography eluting with n-hexane containing 33% ethyl acetate to give 0.89 g of 1-[(4,6-di-t-butyl-5-hydroxy-2-methyl-2,3-dihydrobenzofuran-2-yl)methyl]thiourea as a white crystal (yield 100%).

¹H NMR (270 MHz, CDCl₃) δ ppm: 1.40 (s, 9H), 1.42 (s, 3H), 1.48 (s, 9H), 3.19 (d, 1H, J=16.2 Hz), 3.39 (d, 1H, J=15.2 Hz), 3.78–3.99 (m, 3H), 6.63 (s, 1H). IR (cm⁻¹): 3632, 3440, 3316, 3232, 3084, 2996, 2956, 1606, 1578. Mass: 350 (M⁺).

Example 81
1-Amino-3-[(4,6-di-t-butyl-5-hydroxy-2-methyl-2,3-dihydrobenzofuran-2-yl)methyl]guanidine 1) Synthesis of 1-amino-3-[(5-acetoxy-4,6-di-t-butyl-2-methyl-2,3-dihydrobenzofuran-2-yl)methyl]guanidine To 1.0 g of 1-[(5-acetoxy-4,6-di-t-butyl-2-methyl-2,3-dihydrobenzofuran-2-yl)methyl]thiourea was added 3.62 g of methyl iodide and the mixture was stirred at room temperature for 30 minutes. After reaction, excess methyl iodide was removed using an evaporator. The resulting concentrate was dissolved in 10 ml of methanol and the solution was stirred with 0.3 g of hydrazine monohydrate at room temperature for 2 hours. The reaction solution was combined with water and a saturated aqueous sodium carbonate solution and extracted with ethyl acetate, and the organic layer was washed with saturated brine, dried over anhydrous magnesium sulfate, and then concentrated. The concentrate was purified by silica gel column chromatography eluting with chloroform containing 10% methanol to give 0.98 g of 1-amino-3-[(5-acetoxy-4,6-di-t-butyl-2-methyl-2,3-dihydrobenzofuran-2-yl)methyl]guanidine (rotamer mixture) (yield 99%).

¹H NMR (270 MHz, CDCl₃) δ ppm: 1.28 (s, 4.5H), 1.30 (s, 4.5H), 1.35 (s, 4.5H), 1.37 (s, 4.5H), 1.45 (s, 1.5H), 1.60 (s, 1.5H), 2.30 (s, 1.5H), 2.31 (s, 1.5H), 3.22–3.60 (m, 2H), 3.89 (bs, 2H), 6.75 (s, 0.5H), 6.76 (s, 0.5H). Mass: 391 (M⁺+1).

2) Synthesis of 1-amino-3-[(4,6-di-t-butyl-5-hydroxy-2-methyl-2,3-dihydrobenzofuran-2-yl)methyl]guanidine Under a nitrogen atmosphere, 0.98 g of 1-amino-3-[(5-acetoxy-4,6-di-t-butyl-2-methyl-2,3-dihydrobenzofuran-2-yl)methyl]guanidine was dissolved in 50 ml of toluene. To the solution was added 10 ml of diisobutyl aluminum hydride (1.0 M in toluene) and the mixture was stirred at room temperature for 1 hour. After reaction, a saturated aqueous ammonium chloride solution was added and insoluble matters were filtered off on Celite. The filtrate was extracted with ethyl acetate and the organic layer was washed with saturated brine, dried over anhydrous magnesium sulfate, and then concentrated. The concentrate was purified by silica gel column chromatography eluting with chloroform containing 10% methanol to give 0.32 g of 1-amino-3-[(4,6-di-t-butyl-5-hydroxy-2-methyl-2,3-dihydrobenzofuran-2-yl)methyl]guanidine as a white crystal (yield 37%).

¹H NMR (270 MHz, CDCl₃) δ ppm: 1.40 (s, 9H), 1.43 (s, 3H), 1.49 (s, 9H), 3.26 (d, 1H, J=15.8 Hz), 3.38 (d, 1H, J=15.8 Hz), 3.37 (bs, 2H), 3.67–3.69 (m, 4H), 6.62 (s, 1H). IR (cm⁻¹): 3460, 2964, 1656. Mass: 348 (M⁺).

Example 82
4,6-Di-t-butyl-5-hydroxy-2-methyl-2-(4-nitrophenoxymethyl)-2,3-dihydrobenzofuran 1) Synthesis of 5-acetoxy-4,6-di-t-butyl-2-methyl-2-(4-nitrophenoxymethyl)-2,3-dihydrobenzofuran Under a nitrogen atmosphere, a solution of 3.76 g of 4-nitrophenol in 25 ml of N,N-dimethylformamide was added dropwise to an ice-cooled suspension of 1.08 g of 60% oily sodium hydride in 50 ml of N,N-dimethylformamide, and the mixture was stirred at room temperature for 1 hour. Then, the reaction solution was cooled to 0° C. and a solution of 10 g of 5-acetoxy-4,6-di-t-butyl-2-iodomethyl-2-methyl-2,3-dihydrobenzofuran synthesized in Example 70-2) in 25 ml of N,N-dimethylformamide was added dropwise, and the mixture was heated under reflux for 14 hours. After cooling, the reaction solution was combined with a saturated aqueous ammonium chloride solution and extracted with ethyl acetate, and the organic layer was washed with saturated brine, dried over anhydrous magnesium sulfate, and then concentrated. The concentrate was purified by silica gel column chromatography eluting with n-hexane containing 20% ethyl acetate to give 6.57 g of 5-acetoxy-4,6-di-t-butyl-2-methyl-2-(4-nitrophenoxymethyl)-2,3-dihydrobenzofuran (rotamer mixture) as a pale yellow oil (yield 64%).

¹H NMR (270 MHz, CDCl₃) δ ppm: 1.285 (s, 4.5H), 1.292 (s, 4.5H), 1.38 (s, 9H), 1.57 (s, 1.5H), 1.63 (s, 1.5H), 2.31 (s, 3H), 3.22 (d, 0.5H, J=15.5 Hz), 3.31 (d, 0.5H, J=15.5 Hz), 3.49 (d, 0.5H, J=15.2 Hz), 3.58 (d, 0.5H, J=15.2 Hz), 4.06–4.13 (m, 2H), 6.73 (s, 0.5H), 6.75 (s, 0.5H), 6.95 (d, 1H, J=9.2 Hz), 6.98 (d, 1H, J=8.9 Hz), 8.17 (d, 1H, J=9.2 Hz), 8.19 (d, 1H, J=9.2 Hz). Mass: 455 (M⁺).

2) Synthesis of 4,6-di-t-butyl-5-hydroxy-2-methyl-2-(4-nitrophenoxymethyl)-2,3-dihydrobenzofuran Under a nitrogen atmosphere, 1.0 g of 5-acetoxy-4,6-di-t-butyl-2-methyl-2-(4-nitrophenoxymethyl)-2,3-dihydrobenzofuran was dissolved in 30 ml of toluene. To the solution was added 5.5 ml of diisobutyl aluminum hydride (1.0 M in toluene) and the mixture was stirred at room temperature for 2 hours. After reaction, the reaction solution was combined with a saturated aqueous ammonium chloride solution and 10% hydrochloric acid and extracted with ethyl acetate. The organic layer was washed with saturated brine, dried over anhydrous magnesium sulfate, and then concentrated. The concentrate was purified by silica gel column chromatography eluting with n-hexane containing 5% ethyl acetate to give 0.33 g of 4,6-di-t-butyl-5-hydroxy-2-methyl-2-(4-nitrophenoxymethyl)-2,3-dihydrobenzofuran as a pale yellow oil (yield 36%).

¹H NMR (270 MHz, CDCl₃) δ ppm: 1.48 (s, 9H), 1.58 (s, 9H), 1.66 (s, 3H), 3.36 (d, 1H, J=15.8 Hz), 3.61 (d, 1H, J=15.8 Hz), 4.13 (s, 2H), 4.85 (s, 1H), 6.74 (s, 1H), 7.06 (d, 2H, J=9.2 Hz), 8.26 (d, 2H, J=9.2 Hz). IR (cm⁻¹): 3640, 2956, 1608. Mass: 413 (M⁺).

Example 83
2-(4-Aminophenoxymethyl)-4,6-di-t-butyl-5-hydroxy-2-methyl-2,3-dihydrobenzofuran 1) Synthesis of 5-acetoxy-2-(4-aminophenoxymethyl)-4,6-di-t-butyl-2-methyl-2,3-dihydrobenzofuran A solution of 5.5 g of 5-acetoxy-4,6-di-t-butyl-2-methyl-2-(4-nitrophenoxymethyl)-2,3-dihydrobenzofuran in 50 ml of ethyl acetate was catalytically reduced with 1.1 g of 10% palladium-carbon under a hydrogen atmosphere for 14 hours. After reaction, 10% palladium-carbon was filtered off and the solvent was distilled off to give 5.14 g of 5-acetoxy-2-(4-aminophenoxymethyl)-4,6-di-t-butyl-2-methyl-2,3-dihydrobenzofuran (rotamer mixture) as a colorless oil (yield 100%).

$^1$H NMR (270 MHz, CDCl$_3$) δ ppm: 1.30 (s, 9H), 1.37 (s, 9H), 1.53 (s, 1.5H), 1.60 (s, 1.5H), 2.30 (s, 3H), 3.16 (d, 0.5H, J=15.5 Hz), 3.24 (d, 0.5H, J=15.8 Hz), 3.49 (d, 0.5H, J=15.5 Hz), 3.59 (d, 0.5H, J=15.5 Hz), 3.90 (d, 1H, J=13.5 Hz), 3.91 (d, 1H, J=16.5 Hz), 6.62 (d, 2H, J=8.9 Hz), 6.74 (d, 2H, J=8.9 Hz), 6.78 (s, 1H). Mass: 425 (M$^+$).

2) Synthesis of 2-(4-aminophenoxymethyl)-4,6-di-t-butyl-5-hydroxy-2-methyl-2,3-dihydrobenzofuran Under a nitrogen atmosphere, 1.2 g of 5-acetoxy-2-(4-aminophenoxymethyl)-4,6-di-t-butyl-2-methyl-2,3-dihydrobenzofuran was dissolved in 30 ml of toluene. To the solution was added 11.3 ml of diisobutyl aluminum hydride (1.0 M in toluene) and the mixture was stirred at room temperature for 2 hours. After reaction, a saturated aqueous ammonium chloride solution was added and insoluble matters were filtered off on Celite and the filtrate was extracted with ethyl acetate. The organic layer was washed with saturated brine, dried over anhydrous magnesium sulfate, and then concentrated. The concentrate was purified by silica gel column chromatography eluting with n-hexane containing 33% ethyl acetate to give 0.63 g of 2-(4-aminophenoxymethyl)-4,6-di-t-butyl-5-hydroxy-2-methyl-2,3-dihydrobenzofuran as a pale yellow oil (yield 59%).

$^1$H NMR (270 MHz, CDCl$_3$) δ ppm: 1.40 (s, 9H), 1.49 (s, 9H), 1.54 (s, 3H), 3.21 (d, 1H, J=15.8 Hz), 3.40 (bs, 2H), 3.54 (d, 1H, J=15.8 Hz), 3.87 (s, 2H), 4.73 (s, 1H), 6.62 (d, 2H, J=8.6 Hz), 6.68 (s, 1H), 6.76 (d, 2H, J=8.6 Hz). IR (cm$^{-1}$): 3640, 3456, 3368, 2956, 1614. Mass: 383 (M$^+$).

Example 84
1-{4-[(4,6-Di-t-butyl-5-hydroxy-2-methyl-2,3-dihydrobenzofuran-2-yl)methoxy]phenyl}guanidine 1) Synthesis of 1-{4-[(5-acetoxy-4,6-di-t-butyl-2-methyl-2,3-dihydrobenzofuran-2-yl)methoxy]phenyl}guanidine To a solution of 3.0 g of 5-acetoxy-2-(4-aminophenoxymethyl)-4,6-di-t-butyl-2-methyl-2,3-dihydrobenzofuran in 30 ml of ethanol was added 30 ml of a saturated ethanolic hydrogen chloride and the mixture was stirred at room temperature for 10 minutes. Then, excess hydrogen chloride and ethanol were distilled off using an evaporator to give a hydrochloride. The resulting hydrochloride was dissolved in 100 ml of ethanol again and 10.65 ml of 50% cyanamide was added dropwise at room temperature, and the mixture was heated under reflux for 14 hours. After cooling, ethanol was distilled off using an evaporator and the reaction solution was combined with a 1N aqueous sodium hydroxide solution and extracted with ethyl acetate. The organic layer was washed with saturated brine, dried over anhydrous magnesium sulfate, and then concentrated. The concentrate was purified by silica gel column chromatography eluting with chloroform containing 10% methanol to give 1.41 g of 1-{4-[(5-acetoxy-4,6-di-t-butyl-2-methyl-2,3-dihydrobenzofuran-2-yl)methoxy]phenyl}guanidine (rotamer mixture) as a colorless oil (yield 43%).

$^1$H NMR (270 MHz, CDCl$_3$: CD$_3$OD=9:1) δ ppm: 1.30 (s, 4.5H), 1.305 (s, 4.5H), 1.38 (s, 4.5H), 1.39 (s, 4.5H), 1.55 (s, 1.5H), 1.63 (s, 1.5H), 2.33 (s, 3H), 3,22 (d, 0.5H, J=15.5 Hz), 3.31 (d, 0.5H, J=15.8 Hz), 3.35 (bs, 2H), 3.50 (d, 0.5 Hz, J=15.5 Hz), 3.60 (d, 0.5H, J=15.5 Hz), 3.99 (s, 1H), 4.06 (s, 1H), 6.75 (s, 0.5 Hz), 6.77 (s, 0.5H), 6.97 (d, 1H, J=9.2 Hz), 7.00 (d, 1H, J=9.2 Hz), 7.16 (d, 1H, J=8.9 Hz), 7.19 (d, 1H, J=8.9 Hz). Mass: 467 (M$^+$).

2) Synthesis of 1-{4-[(4,6-di-t-butyl-5-hydroxy-2-methyl-2,3-dihydrobenzofuran-2-yl)methoxy]phenyl}guanidine Under a nitrogen atmosphere, 1.4 g of 1-{4-[(5-acetoxy-4,6-di-t-butyl-2-methyl-2,3-dihydrobenzofuran-2-yl)methoxy]phenyl}guanidine was dissolved in 50 ml of toluene. To the solution was added 12 ml of diisobutyl aluminum hydride (1.0 M in toluene) and the mixture was stirred at room temperature for 14 hours. After further addition of 6 ml of diisobutyl aluminum hydride (1.0 M in toluene) at room temperature, the mixture was heated under reflux for 2 hours. After reaction, a saturated aqueous ammonium chloride solution was added, and insoluble matters were filtered off on Celite and the filtrate was extracted with ethyl acetate. The organic layer was washed with saturated brine, dried over anhydrous magnesium sulfate, and then concentrated. The concentrate was purified by silica gel column chromatography eluting with chloroform containing 10% methanol to give 0.67 g of 1-{4-[(4,6-di-t-butyl-5-hydroxy-2-methyl-2,3-dihydrobenzofuran-2-yl)methoxy]phenyl}guanidine as a pale yellow oil (yield 52%).

$^1$H NMR (270 MHz, CDCl$_3$) δ ppm: 1.40 (s, 9H), 1.49 (s, 9H), 1.55 (s, 3H), 3.25 (d, 1H, J=15.8 Hz), 3.52 (d, 1H, J=15.5 Hz), 3.94 (bs, 2H), 4.77 (s, 1H), 6.67 (s, 1H), 6.95 (d, 2H, J=8.9 Hz), 7.15 (d, 2H, J=8.6 Hz). IR (cm$^{-1}$): 3644, 3336, 2956, 1666. Mass: 425 (M$^+$).

Example 85
1-{4-[(4,6-Di-t-butyl-5-hydroxy-2-methyl-2,3-dihydrobenzofuran-2-yl)methoxy]benzylideneamino}guanidine 1) Synthesis of 5-acetoxy-4,6-di-t-butyl-2-(4-formylphenoxymethyl)-2-methyl-2,3-dihydrobenzofuran Under a nitrogen atmosphere, a solution of 4.57 g of 4-hydroxybenzaldehyde in 70 ml of N,N-dimethylformamide was added dropwise to an ice-cooled suspension of 1.5 g of 60% oily sodium hydride in 50 ml of N,N-dimethylformamide and the mixture was stirred at room temperature for 30 minutes. Then, the reaction solution was cooled to 0° C. and a solution of 13.2 g of 5-acetoxy-4,6-di-t-butyl-2-iodomethyl-2-methyl-2,3-dihydrobenzofuran synthesized in Example 70-2) in 100 ml of N,N-dimethylformamide was added dropwise, and the mixture was heated under reflux for 6 hours. After cooling, the reaction solution was combined with a saturated aqueous ammonium chloride solution and extracted with ethyl acetate, and the organic layer was washed with saturated brine, dried over anhydrous magnesium sulfate, and then concentrated. The concentrate was purified by silica gel column chromatography eluting with n-hexane containing 20% ethyl acetate to give 6.4 g of 5-acetoxy-4,6-di-t-butyl-2-(4-formylphenoxymethyl)-2-methyl-2,3-dihydrobenzofuran (rotamer mixture) as a colorless oil (yield 48%).

$^1$H NMR (270 MHz, CDCl$_3$) δ ppm: 1.30 (s, 9H), 1.38 (s, 4.5H), 1.39 (s, 4.5H), 1.57 (s, 1.5H), 1.63 (s, 1.5H), 2.31 (s, 3H), 3.22 (d, 0.5H, J=15.8 Hz), 3.30 (d, 0.5H, J=15.8 Hz), 3.49 (d, 0.5H, J=15.8 Hz), 3.60 (d, 0.5H, J=15.8 Hz), 4.08 (dd, 2H, J=16.2 Hz, J=13.5 Hz), 6.76 (s, 0.5H), 6.77 (s, 0.5H), 7.00 (d, 1H, J=8.6 Hz), 7.03 (d, 1H, J=8.6 Hz), 7.82 (d, 1H, J=8.6 Hz), 7.83 (d, 1H, J=8.6 Hz), 9.88 (s, 0.5H), 9.89 (s, 0.5H). Mass: 438 (M$^+$).

2) Synthesis of 1-{4-[(5-acetoxy-4,6-di-t-butyl-2-methyl-2,3-dihydrobenzofuran-2-yl)methoxy]benzylideneamino}guanidine In a mixed solvent of 40 ml of ethanol and 16 ml of pyridine was dissolved 8.54 g of 5-acetoxy-4,6-di-t-butyl- 2-(4-formylphenoxymethyl)-2-methyl-2,3-dihydrobenzofuran and 2.38 g of aminoguanidine hydrochloride was added at room temperature. After heating under reflux for 14 hours and then cooling, ethanol and excess pyridine were distilled off using an evaporator and the concentrate was combined with water and extracted with ethyl acetate, and the organic layer was washed with saturated brine, dried over anhydrous magnesium sulfate, and then concentrated. The concentrate was purified by silica gel column chromatography eluting with chloroform containing 5% methanol to give 9.31 g of 1-{4-[(5-acetoxy-4,6-di-t-butyl-2-methyl-2,3-dihydrobenzofuran-2-yl)methoxy]benzylideneamino}guanidine (rotamer mixture) as a pale yellow oil (yield 97%).

$^1$H NMR (270 MHz, CDCl$_3$) δ ppm: 1.29 (s, 9H), 1.37 (s, 9H), 1.40 (s, 1.5H), 1.49 (s, 1.5H), 2.31 (s, 3H), 3.20 (d, 0.5H, J=15.8 Hz), 3.28 (d, 0.5H, J=15.5 Hz), 3.48 (d, 0.5H, J=15.5 Hz), 3.58 (d, 0.5H, J=15.5 Hz), 4.00 (d, 1H, J=13.5 Hz), 4.01 (d, 1H, J=15.5 Hz), 6.77 (s, 1H), 6.89 (d, 1H, J=8.6 Hz), 6.92 (d, 1H, J=8.3 Hz), 7.55 (d, 1H, J=8.9 Hz), 7.56 (d, 1H, J=8.6 Hz), 8.04 (s, 0.5H), 8.05 (s, 0.5H). Mass: 494 (M$^+$).

3) Synthesis of 1-{4-[(4,6-di-t-butyl-5-hydroxy-2-methyl-2,3-dihydrobenzofuran-2-yl)methoxy]benzylideneamino}guanidine Under a nitrogen atmosphere, 2.0 g of 1-{4-[(5-acetoxy-4,6-di-t-butyl-2-methyl-2,3-dihydrobenzofuran-2-yl)methoxy]benzylideneamino}guanidine was dissolved in 100 ml of tetrahydrofuran, and 10 ml of n-butyl lithium (1.6 M in n-hexane) was added and the mixture was stirred at room temperature for 30 minutes. After reaction, the reaction solution was combined with a saturated aqueous ammonium chloride solution and extracted with ethyl acetate, and the organic layer was washed with saturated brine, dried over anhydrous magnesium sulfate, and then concentrated. The concentrate was purified by silica gel column chromatography eluting with chloroform containing 10% methanol to give 0.46 g of 1-{4-[(4,6-di-t-butyl-5-hydroxy-2-methyl-2,3-dihydrobenzofuran-2-yl)methoxy]benzylideneamino}guanidine as a pale yellow solid (yield 25%).

$^1$H NMR (270 MHz, CDCl$_3$) δ ppm: 1.40 (s, 9H), 1.49 (s, 9H), 1.55 (s, 3H), 3.24 (d, 1H, J=15.8 Hz), 3.52 (d, 1H, J=15.5 Hz), 3.96 (s, 2H), 4.79 (s, 1H), 6.67 (s, 1H), 6.90 (d, 2H, J=8.6 Hz), 7.54 (d, 2H, J=8.6 Hz), 8.00 (s, 1H). IR (cm$^{-1}$): 3644, 3344, 2956, 1670, 1632. Mass: 452 (M$^+$).

Example 86

1-{4-[(4,6-Di-t-butyl-5-hydroxy-2-methyl-2,3-dihydrobenzofuran-2-yl)methoxy]benzylamino}guanidine Under a nitrogen atmosphere, a solution of 1.0 g of 1-{4-[(5-aceoxy-4,6-di-t-butyl-2-methyl-2,3-dihydrobenzofuran-2-yl)methoxy]benzylideneamino}guanidine in 15 ml of tetrahydrofuran was added dropwise to a suspension of 0.3 g of lithium aluminum hydride in 15 ml of tetrahydrofuran at room temperature. After heating under reflux for 4 hours, the solution was cooled to room temperature and 0.15 g of lithium aluminum hydride was carefully added, and the mixture was heated under reflux again for 4 hours. After reaction, a saturated aqueous ammonium chloride solution was added under ice-cooling and insoluble matters were filtered off on Celite, and the filtrate was extracted with ethyl acetate. The organic layer was dried over anhydrous magnesium sulfate and then concentrated. The concentrate was purified by silica gel column chromatography eluting with chloroform containing 10% methanol to give 0.59 g of 1-{4-[(4,6-di-t-butyl-5-hydroxy-2-methyl-2,3-dihydrobenzofuran-2-yl)methoxy]benzylamino}guanidine as a pale yellow solid (yield 65%).

$^1$H NMR (270 MHz, CDCl$_3$) δ ppm: 1.41 (s, 9H), 1.51 (s, 9H), 1.55 (s, 3H), 3.25 (d, 1H, J=16.2 Hz), 3.54 (d, 1H, J=15.5 Hz), 3.80–3.90 (m, 2H), 3.93 (s, 2H), 4.77 (s, 1H), 6.68 (s, 1H), 6.87 (d, 2H, J=8.3 Hz), 7.23 (d, 2H, J=8.3 Hz). IR (cm$^{-1}$): 3644, 3248, 2956, 1654. Mass: 454 (M$^+$).

Example 87

1-[(4,6-Di-t-butyl-5-hydroxy-2-methyl-2,3-dihydrobenzofuran-2-yl)methylamino]guanidine 1) Synthesis of 5-acetoxy-4,6-di-t-butyl-2-formyl-2-methyl-2,3-dihydrobenzofuran Under a nitrogen atmosphere, 2.64 ml of oxalyl chloride was added to 40 ml of dichloromethane and the mixture was cooled to −78° C. Then, a solution of 3.62 ml of dimethyl sulfoxide in 10 ml of dichloromethane was added dropwise at −78° C. and the mixture was stirred for 30 minutes. A solution of 5.4 g of 5-acetoxy-4,6-di-t-butyl-2-hydroxymethyl-2-methyl-2,3-dihydrobenzofuran synthesized in Example 47 in 15 ml of dichloromethane was added dropwise and the mixture was stirred again at −78° C. for 1 hour. The mixture was combined with 15.3 ml of triethylamine and allowed to warm to room temperature over 1 hour. After reaction, the reaction solution was combined with a saturated aqueous ammonium chloride solution and extracted with ethyl acetate. The organic layer was dried over anhydrous magnesium sulfate and then concentrated. The concentrate was purified by silica gel column chromatography eluting with n-hexane containing 20% ethyl acetate to give 3.95 g of 5-acetoxy-4,6-di-t-butyl-2-formyl-2-methyl-2,3-dihydrobenzofuran (rotamer mixture) as a white crystal (yield 71%).

$^1$H NMR (270 MHz, CDCl$_3$) δ ppm: 1.31 (s, 9H), 1.36 (s, 9H), 1.51 (s, 1.5H), 1.54 (s, 1.5H), 2.30 (s, 3H), 3.16 (d, 0.5H, J=15.8 Hz), 3.25 (d, 0.5H, J=15.8 Hz), 3.68 (d, 0.5H, J=15.8 Hz), 3.76 (d, 0.5H, J=15.8 Hz), 6.86 (s, 0.5H), 6.87 (s, 0.5H), 9.74 (s, 0.5H), 9.76 (s, 0.5H). Mass: 332 (M$^+$).

2) Synthesis of 1-[(5-acetoxy-4,6-di-t-butyl-2-methyl-2,3-dihydrobenzofuran-2-yl)methylideneamino]guanidine In a mixed solvent of 20 ml of ethanol and 8 ml of pyridine was dissolved 3.9 g of 5-acetoxy-4,6-di-t-butyl-2-formyl-2-methyl-2,3-dihydrobenzofuran, and 1.42 g of aminoguanidine hydrochloride was added at room temperature. After heating under reflux for 14 hours and then cooling, ethanol and excess pyridine were distilled off using an evaporator, and the concentrate was combined with water and extracted with ethyl acetate. The organic layer was washed with saturated brine, dried over anhydrous magnesium sulfate, and then concentrated. The concentrate was purified by silica gel column chromatography eluting with chloroform containing 10% methanol to give 4.48 g of 1-[(5-acetoxy-4,6-di-t-butyl-2-methyl-2,3-dihydrobenzofuran-2-yl)methylideneamino]guanidine (rotamer mixture) as a pale yellow oil (yield 99%).

$^1$H NMR (270 MHz, CDCl$_3$) δ ppm: 1.29 (s, 4.5H), 1.30 (s, 4.5H), 1.36 (s, 4.5H), 1.37 (s, 4.5H), 1.59 (s, 1.5H), 1.64 (s, 1.5H), 2.29 (s, 1.5H), 2.30 (s, 1.5H), 3.23 (d, 0.5H, J=15.8 Hz), 3.29 (d, 0.5H, J=16.2 Hz), 3.70 (d, 0.5H, J=12.9 Hz), 3.75 (d, 0.5H, J=15.5 Hz), 3.928 (d, 1H, J=8.6 Hz), 3.933 (d, 1H, J=5.9 Hz), 6.757 (s, 0.5H), 6.764 (s, 0.5H), 7.54 (s, 0.5H), 7.60 (s, 0.5H). Mass: 389 (M$^+$+1).

3) Synthesis of 1-[(4,6-di-t-butyl-5-hydroxy-2-methyl-2,3-dihydrobenzofuran-2-yl)methylamino]guanidine Under a nitrogen atmosphere, a solution of 1.0 g of 1-[(5-acetoxy-4,6-di-t-butyl-2-methyl-2,3-dihydrobenzofuran-2-yl)methylideneamino]guanidine in 10 ml of tetrahydrofuran was added dropwise to a suspension of 0.98 g of lithium aluminum hydride in 20 ml of tetrahydrofuran at room temperature. After heating under reflux for 14 hours, a saturated aqueous ammonium chloride was added under ice-cooling, insoluble matters were filtered off on Celite and the filtrate was extracted with ethyl acetate. The organic layer was dried over anhydrous magnesium sulfate and then concentrated. The concentrate was purified by silica gel column chromatography eluting with chloroform containing 10% methanol to give 0.68 g of 1-[(4,6-di-t-butyl-5-hydroxy-2-methyl-2,3-dihydrobenzofuran-2-yl)methylamino]guanidine as a pale yellow oil (yield 76%).

$^1$H NMR (270 MHz, CDCl$_3$) δ ppm: 1.40 (s, 9H), 1.43 (s, 3H), 1.47 (s, 9H), 3.03 (bs, 2H), 3.20 (d, 1H, J=15.8 Hz), 3.34 (d, 1H, J=15.5 Hz), 4.77 (s, 1H), 6.63 (s, 1H). IR (cm$^{-1}$): 3644, 3256, 2956, 1666. Mass: 348 (M$^+$).

The structural formulae of the above compounds are shown in tables 1–8 below.

TABLE 1

| Ex. No. | R$_1$ | R$_2$ | X | R$_5$ | R$_6$ |
|---|---|---|---|---|---|
| 1 | H | H | O | H | H |
| 2 | H | H | O | Me | H |
| 3 | Ac | H | O | Me | Me |
| 4 | H | H | O | Me | Me |
| 5 | Ac | H | O | Et | Et |
| 6 | H | H | O | Et | Et |
| 7 | H | H | O | n-Pr | n-Pr |
| 8 | H | H | O | n-Bu | n-Bu |
| 12 | H | H | O | n-Octyl | H |
| 13 | H | H | O | t-Bu | H |
| 14 | H | H | O | i-Pr | i-Pr |
| 15 | H | H | O | Ph | Ph |
| 16 | H | H | O | CH$_2$Ph | CH$_2$Ph |
| 17 | H | H | O | CH$_2$Cl | H |

TABLE 2

| Ex. No. | R$_1$ | R$_2$ | X | R$_5$ | R$_6$ |
|---|---|---|---|---|---|
| 18 | H | H | O | cyclopentyl (spiro) | |
| 19 | H | H | O | cyclohexyl (spiro) | |
| 20 | H | H | O | cycloheptyl (spiro) | |

TABLE 2-continued

| Ex. No. | R$_1$ | R$_2$ | X | R$_5$ | R$_6$ |
|---|---|---|---|---|---|
| 21 | H | H | O | cyclooctyl (spiro) | |
| 22 | H | H | O | tetrahydropyranyl (spiro) | |
| 24 | Ac | n-Pr | O | Me | Me |
| 25 | H | n-Pr | O | Me | Me |
| 36 | H | H | O | n-Pentyl | n-Pentyl |
| 37 | H | H | O | n-Octyl | n-Octyl |
| 38 | H | H | O | n-Heptyl | n-Heptyl |
| 39 | H | H | O | n-Hexyl | n-Hexyl |
| 40 | Ac | H | O | Isoamyl | Isoamyl |
| 41 | H | H | O | Isoamyl | Isoamyl |

TABLE 3

| Ex. No. | R$_1$ | R$_2$ | X | R$_5$ | R$_6$ |
|---|---|---|---|---|---|
| 42 | Ac | H | O | -(CH$_2$)$_3$-CH=C(CH$_3$)-CH$_3$ | Me |
| 43 | H | H | O | -(CH$_2$)$_3$-CH=C(CH$_3$)-CH$_3$ | Me |
| 44 | H | H | O | -(CH$_2$)$_3$-CH=C(CH$_3$)-CH$_3$ | Me |
| 45 | Ac | H | O | -(CH$_2$)$_3$-CH=C(CH$_3$)-CH$_2$OH | Me |
| 46 | H | H | O | -(CH$_2$)$_3$-CH=C(CH$_3$)-CH$_2$OH | Me |

TABLE 3-continued

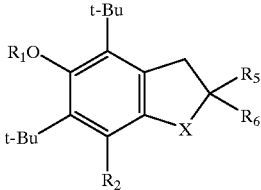

| Ex. No. | $R_1$ | $R_2$ | X | $R_5$ | $R_6$ |
|---|---|---|---|---|---|
| 47 | Ac | H | O | $CH_2OH$ | Me |
| 48 | H | H | O | $CH_2OH$ | Me |
| 49 | Ac | H | S | n-Pentyl | n-Pentyl |
| 50 | H | H | S | n-Pentyl | n-Pentyl |
| 51 | H | H | S | Me | H |
| 52 | H | H | S | Me | Me |
| 56 | Ac | H | $SO_2$ | H | H |

TABLE 4

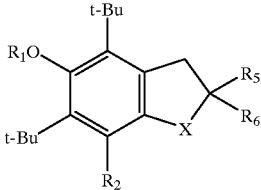

| Ex. No. | $R_1$ | $R_2$ | X | $R_5$ | $R_6$ |
|---|---|---|---|---|---|
| 57 | H | H | S | H | H |
| 58 | H | H | S |  | |
| 59 | Ac | H | S | $CH_2I$ | Me |
| 60 | Ac | H | S | $CH_2N(CH_3)_2$ | Me |
| 61 | H | H | S | $CH_2N(CH_3)_2$ | Me |
| 62 | Ac | H | S | $CH_2OAc$ | Me |
| 63 | H | H | S | $CH_2OH$ | Me |
| 64 | H | H | S | 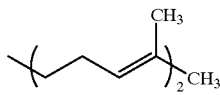 | Me |
| 65 | H | H | S | 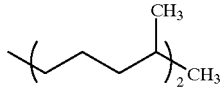 | Me |
| 66 | H | H | S | 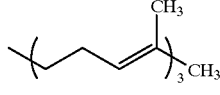 | Me |
| 67 | H | H | S | 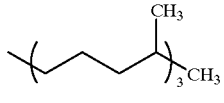 | Me |

TABLE 5

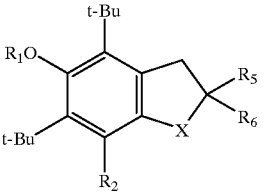

| Ex. No. | $R_1$ | $R_2$ | X | $R_5$ | $R_6$ |
|---|---|---|---|---|---|
| 68 | H | H | O | 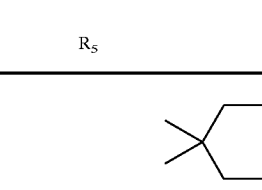 | |
| 69 | H | H | S | 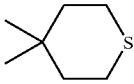 | |
| 70 | H | H | O | $CH_2NH_2$ | Me |
| 71 | H | H | O | Me | $CH_2CN$ |
| 72 | H | H | O | Me | $CO_2H$ |
| 73 | H | H | O | Me | $CO_2Me$ |
| 74 | H | H | O | Me |  |
| 75 | H | H | O | Me |  |
| 76 | H | H | O | Me | 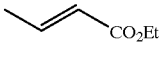 |
| 77 | H | H | O | Me | 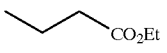 |
| 78 | H | H | O | Me | 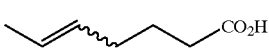 |
| 79 | H | H | O | Me | 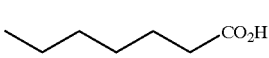 |
| 80 | H | H | O | Me | 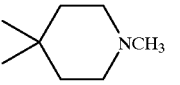 |

TABLE 6
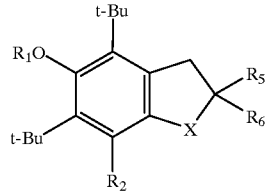
| Ex. No. | R₁ | R₂ | X | R₅ | R₆ |
|---|---|---|---|---|---|
| 81 | H | H | O | Me | 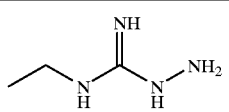 |
| 82 | H | H | O | Me | 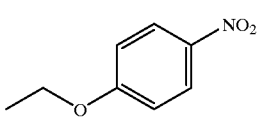 |
| 83 | H | H | O | Me | 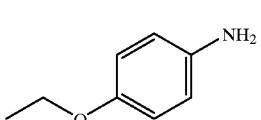 |
| 84 | H | H | O | Me | 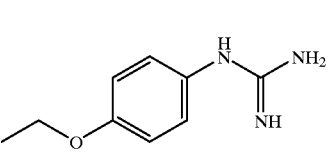 |
| 85 | H | H | O | Me | 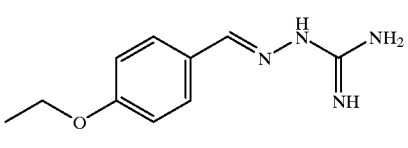 |
| 86 | H | H | O | Me | 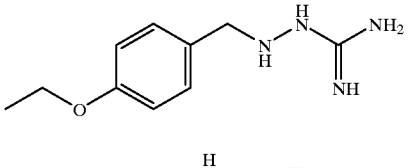 |
| 87 | H | H | O | Me | 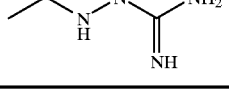 |
TABLE 7
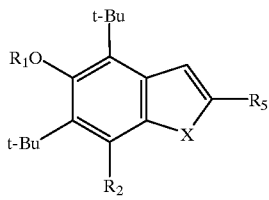
| Ex. No. | R₁ | R₂ | X | R₅ |
|---|---|---|---|---|
| 9 | Ac | H | O | 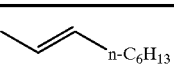 n-C₆H₁₃ |
TABLE 7-continued
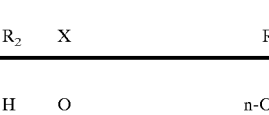
| Ex. No. | R₁ | R₂ | X | R₅ |
|---|---|---|---|---|
| 10 | Ac | H | O | n-Octyl |

TABLE 7-continued
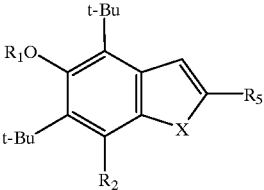
| Ex. No. | R₁ | R₂ | X | R₅ |
|---|---|---|---|---|
| 11 | H | H | O | n-Octyl |
| 26 | Ac | H | O | H |
| 27 | H | H | O | H |
| 28 | H | H | O | Me |
| 29 | H | H | O | t-Bu |
| 53 | Ac | H | S | H |
| 54 | H | H | S | H |
| 55 | Ac | H | SO₂ | H |
TABLE 8
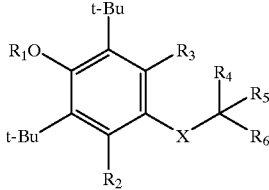
| Ex. No. | R₁ | R₂ | R₃ | X | R₄ | R₅ | R₆ |
|---|---|---|---|---|---|---|---|
| 23 | Ac | n-Pr | H | O | 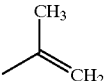 | H | H |
| 30 | Ac | Me | H | O | Et | H | H |
| 31 | H | Me | H | O | Et | H | H |
| 32 | Ac | Me | H | O | Vinyl | H | H |
| 33 | H | Me | H | O | Vinyl | H | H |
| 34 | Ac | Me | H | O | 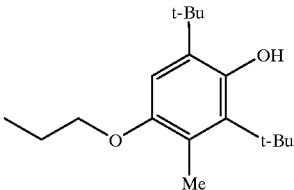 | H | H |
| 35 | H | Me | H | O | 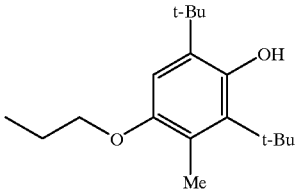 | H | H |

Test Example 1
Protective Effect Against Cell Injury of Porcine Kidney-Derived LLC-PK1 Cells (1)

For the purpose of evaluating in vitro cytoprotective effect of the compounds of the present invention, a cytoprotective study was performed using porcine kidney-derived LLC-PK1 cells (ATCC-CRL-13921) injured by oxidized low-density lipoprotein (oxidized LDL).

Oxidized LDL was prepared by incubating 1 mg/ml of rabbit LDL in PBS (−) in the presence of 10 μM $CuSO_4$ at 37° C. for 24 hours. Cell culture was carried out by plating $1.25 \times 10^4$ cells/250 μl/well on a 48-well plate containing M199 medium containing 3% FBS. Test compounds were dissolved or suspended in ethanol and added to the wells in an amount of 1.25 μl/well to a concentration of 0.1, 1 or 10 μM in each well. After 16 hours or immediately after the addition of the compounds, oxidized LDL was added to the wells. Probucol, α-tocopherol and Trolox which is a water-soluble analogue of α-tocopherol were used as reference control compounds. Oxidized LDL was diluted twice with saline and then added to the wells in an amount of 62.5 μl/well to a concentration of 100 μg/ml and the cells were cultured for 6 hours after addition of the oxidized LDL. Then, 162.5 μl/well of the culture medium were collected and measured for the lactate dehydrogenase (LDH) level (LD-L: SIGNA DIAGNOSTICS) having leaked into the medium.

The magnitude of cytoprotective effect was expressed as the cytoprotection rate which was determined by calculating the data assuming that the magnitude in wells containing oxidized LDL is 0% and that the magnitude in wells containing saline is 100%.

The results are shown in Table 9.

As shown in Table 9, the compounds of the present invention inhibit cell injury induced by oxidized LDL.

Test Example 2

Protective Effect Against Cell Injury of Porcine Kidney-Derived LLC-PK1 Cells (2)

For the purpose of evaluating in vitro cytoprotective effect of the compounds of the present invention, a cytoprotective study was performed using porcine kidney-derived LLC-PK1 cells (ATCC-CRL-13921) injured by oxidized low-density lipoprotein (oxidized LDL) in the same manner as in Test example 1 with the exception of some points.

Preparation of oxidized LDL and the conditions for cell culture and addition of test compounds were the same as in Test example 1. However, oxidized LDL was not diluted with saline and added to cells in an amount of 25 μl/well to a concentration of 91 μg/ml and the cells were cultured for 6 hours after addition of the oxidized LDL. Then, 150 μl/well of the culture medium were collected and measured for the lactate dehydrogenase (LDH) level (LD-L: SIGMA DIAGNOSTICS) having leaked in the medium. The results are shown in Table 10.

TABLE 9

Protective effect against oxidized LDL-induced injury of porcine kidney-derived LLC-PK1 cells (1)

| Ex. No. of Compound | Cytoprotection rate (%): Compound added 16 hours before adding oxidized LDL | | | Cytoprotection rate (%): Compound added immediately before adding oxidized LDL | | |
|---|---|---|---|---|---|---|
| | 0.1 μM | 1 μM | 10 μM | 0.1 μM | 1 μM | 10 μM |
| 1 | 22.3 ± 2.8 | 103.9 ± 3.3 | 100.9 ± 0.5 | 7.6 ± 1.4 | 99.7 ± 0.4 | 100.9 ± 0.3 |
| 3 | 27.0 ± 18.2 | 1.8 ± 6.8 | 23.2 ± 11.3 | −6.5 ± 2.7 | −4.0 ± 5.4 | 4.3 ± 3.6 |
| 4 | 11.5 ± 8.0 | 106.0 ± 1.2 | 100.4 ± 0.3 | −9.6 ± 2.2 | 103.4 ± 4.5 | 99.6 ± 0.8 |
| 13 | 32.0 ± 2.8 | 55.6 ± 15.0 | 99.9 ± 0.2 | 11.9 ± 1.9 | 97.8 ± 2.9 | 100.4 ± 0.4 |
| 16 | 12.0 ± 7.5 | 94.5 ± 4.9 | 98.3 ± 0.3 | −36.7 ± 6.6 | 74.4 ± 6.4 | 99.6 ± 0.1 |
| 18 | −1.9 ± 17.3 | 66.8 ± 22.2 | 99.9 ± 0.2 | −4.5 ± 6.3 | 98.4 ± 0.8 | 99.7 ± 0.2 |
| 20 | −11.3 ± 8.5 | 98.6 ± 1.2 | 105.6 ± 1.2 | −15.8 ± 8.0 | 99.9 ± 0.3 | 101.9 ± 4.7 |
| 22 | 3.5 ± 10.4 | 102.2 ± 0.2 | 101.0 ± 0.5 | −1.7 ± 0.2 | 101.2 ± 1.7 | 101.1 ± 0.2 |
| 25 | 47.4 ± 6.0 | 7.9 ± 10.8 | 28.6 ± 6.4 | 1.4 ± 3.8 | 0.8 ± 7.7 | 66.5 ± 7.7 |
| 27 | 44.1 ± 24.3 | 96.0 ± 0.7 | 97.7 ± 1.7 | 4.2 ± 1.4 | 91.0 ± 7.4 | 96.8 ± 0.5 |
| 31 | −0.1 ± 18.7 | 3.5 ± 18.5 | 68.8 ± 15.8 | 6.9 ± 1.1 | 15.7 ± 5.3 | 71.8 ± 6.9 |
| 36 | −1.0 ± 7.4 | 92.2 ± 3.7 | 97.7 ± 1.1 | −3.2 ± 1.1 | 0.6 ± 4.2 | 78.8 ± 3.6 |
| 46 | 11.0 ± 1.5 | 53.5 ± 10.0 | 103.5 ± 2.0 | −8.9 ± 3.1 | 101.0 ± 1.3 | 104.4 ± 0.4 |
| 48 | −0.5 ± 23.4 | 84.2 ± 4.4 | 98.1 ± 0.7 | 3.8 ± 0.3 | 101.8 ± 2.5 | 98.2 ± 0.3 |
| 50 | 1.9 ± 8.0 | 37.4 ± 17.1 | 81.6 ± 4.0 | 9.3 ± 3.3 | 15.3 ± 0.8 | 99.2 ± 1.3 |
| 51 | −6.1 ± 7.6 | 17.8 ± 18.1 | 99.3 ± 0.7 | 2.2 ± 4.9 | 28.9 ± 15.7 | 101.4 ± 0.3 |
| 52 | 6.5 ± 1.4 | 41.2 ± 11.9 | 99.1 ± 0.1 | −0.7 ± 1.1 | 96.9 ± 1.2 | 99.5 ± 0.4 |
| 54 | 96.0 ± 0.5 | 90.0 ± 5.0 | 94.8 ± 2.2 | 35.9 ± 26.4 | 96.7 ± 0.2 | 98.9 ± 0.4 |
| 58 | 3.6 ± 18.3 | 95.0 ± 4.2 | 99.3 ± 0.9 | 11.0 ± 4.0 | 74.3 ± 19.2 | 101.0 ± 0.2 |
| α-tocopherol | 7.2 ± 2.2 | 72.1 ± 13.8 | 98.9 ± 1.0 | −2.8 ± 1.5 | 8.2 ± 5.7 | 2.7 ± 2.3 |
| Trolox | 0.4 ± 1.3 | 6.4 ± 10.6 | 17.5 ± 16.9 | 0.0 ± 0.6 | −7.1 ± 5.7 | −4.9 ± 6.3 |
| Probucol | 22.5 ± 15.1 | 36.4 ± 13.3 | 99.7 ± 1.1 | −1.8 ± 9.7 | 0.3 ± 11.3 | 17.0 ± 7.8 |

Each value represents mean ± standard deviation.

TABLE 10

Protective effect against oxidized LDL-induced injury of porcine kidney-derived LLC-PK1 cells (2)

| Ex. No. of Compound | Cytoprotection rate (%): Compound added 16 hours before adding oxidized LDL | | | Cytoprotection rate (%): Compound added immediately before adding oxidized LDL | | |
|---|---|---|---|---|---|---|
| | 0.1 µM | 1 µM | 10 µM | 0.1 µM | 1 µM | 10 µM |
| 19 | 2.7 ± 1.6 | 60.6 ± 6.1 | 102.7 ± 1.2 | 1.2 ± 0.9 | 86.8 ± 5.2 | 101.0 ± 2.5 |
| 21 | 15.6 ± 3.6 | 13.7 ± 13.4 | 16.0 ± 2.6 | 2.5 ± 2.5 | 6.1 ± 1.9 | 14.4 ± 3.9 |
| 61 | 5.0 ± 1.2 | 85.7 ± 8.1 | 101.3 ± 0.6 | 5.1 ± 1.5 | 97.6 ± 1.8 | 101.7 ± 0.5 |
| 63 | 4.2 ± 4.4 | 95.3 ± 3.6 | 100.2 ± 0.4 | 5.9 ± 1.7 | 97.3 ± 2.9 | 101.1 ± 0.2 |
| 68 | 12.0 ± 3.6 | 56.2 ± 4.6 | 102.1 ± 1.5 | 6.3 ± 3.3 | 85.8 ± 8.6 | 100.6 ± 0.2 |
| 69 | 1.0 ± 4.7 | 24.6 ± 12.8 | 100.4 ± 0.5 | 4.5 ± 2.1 | 42.5 ± 6.3 | 101.6 ± 0.7 |
| 70 | 17.5 ± 2.2 | 101.0 ± 0.7 | 100.7 ± 0.8 | 9.9 ± 2.4 | 100.6 ± 0.9 | 101.3 ± 0.6 |
| 71 | 10.4 ± 2.2 | 26.9 ± 2.5 | 105.6 ± 0.6 | 4.3 ± 4.1 | 80.2 ± 10.3 | 107.0 ± 2.0 |
| 72 | 2.3 ± 1.3 | 14.8 ± 2.0 | 95.9 ± 1.3 | 2.7 ± 4.3 | 14.0 ± 3.3 | 95.2 ± 0.9 |
| 73 | 5.7 ± 1.4 | 78.9 ± 16.9 | 99.7 ± 1.4 | 4.8 ± 2.9 | 97.8 ± 1.6 | 99.4 ± 0.3 |
| 74 | 25.2 ± 3.3 | 54.8 ± 3.8 | 103.6 ± 0.5 | 10.1 ± 2.3 | 72.7 ± 4.7 | 103.5 ± 0.6 |
| 75 | 4.9 ± 2.7 | 26.6 ± 7.0 | 99.8 ± 0.9 | −4.9 ± 1.8 | 51.8 ± 4.2 | 98.7 ± 0.4 |
| 76 | −10.4 ± 4.2 | −2.8 ± 3.5 | 13.8 ± 4.2 | −12.8 ± 1.2 | −7.6 ± 2.2 | 58.8 ± 9.5 |
| 77 | 12.3 ± 2.7 | 6.1 ± 1.5 | 35.8 ± 4.0 | 9.1 ± 1.8 | 10.6 ± 1.5 | 48.5 ± 2.1 |
| 78 | −2.8 ± 0.9 | −10.7 ± 8.9 | 67.5 ± 6.1 | −11.6 ± 2.7 | −6.7 ± 2.8 | 80.9 ± 1.5 |
| 80 | 9.2 ± 1.8 | 23.7 ± 5.8 | 102.4 ± 0.5 | −1.3 ± 1.4 | 10.7 ± 2.1 | 102.6 ± 1.0 |
| 81 | 6.9 ± 3.1 | 4.2 ± 5.1 | 101.1 ± 0.1 | 8.8 ± 1.6 | 37.8 ± 44.1 | 101.3 ± 0.1 |
| 86 | −0.4 ± 1.9 | 3.6 ± 5.8 | 40.0 ± 2.2 | −0.7 ± 2.3 | 0.2 ± 3.6 | 102.5 ± 0.5 |
| 87 | −7.8 ± 4.4 | 6.5 ± 5.2 | 103.6 ± 0.5 | −0.3 ± 0.5 | 28.6 ± 7.9 | 101.8 ± 0.6 |

Each value represents mean ± standard deviation.

As shown in Table 10, the compounds of the present invention inhibit cell injury induced by oxidized LDL.

Test Example 3

Protective Effect Against Cell Injury of Murine Mesangial Cells (in vitro)

For the purpose of evaluating in vitro cytoprotective effect of the compounds of the present invention on mesangial cells, a cytoprotective study was performed using murine mesangial derived MES13 cells (ATCC-CRL-1927) injured by oxidized LDL.

Oxidized LDL was prepared in the same manner as in Test example 1. Cell culture was carried out by plating $2.5 \times 10^4$ cells/250 µl/well on a 48-well plate using FBS-free medium (mixture of DME medium and F12 medium in a ratio of 3:1). Test compounds were dissolved or suspended in ethanol and added to the wells in an amount of 1.25 µl/well to a concentration of 1 or 10 µM in each well. After 16 hours or immediately after the addition of the compounds, oxidized LDL was added to cells in an amount of 25 µl/well to a concentration of 91 µg/ml and the cells were cultured for 10 hours after addition of the oxidized LDL. Then, 150 µl/well of the culture medium were collected and measured for the lactate dehydrogenase level (LDL: SIGMA DIAGNOSTICS) having leaked in the medium.

The magnitude of cytoprotective effect was expressed as the cytoprotection rate which was determined by calculating the data assuming that the magnitude in wells containing oxidized LDL is 0% and that the magnitude in containing saline is 100%.

The results are shown in Table 11.

TABLE 11

Protective effect against oxidized LDL-induced injury of murine mesangial cells (in vitro)

| Ex. No. of Compound | Cytoprotection rate (%): Compound added 16 hours before adding oxidized LDL | | Cytoprotection rate (%): Compound added immediately before adding oxidized LDL | |
|---|---|---|---|---|
| | 1 µM | 10 µM | 1 µM | 10 µM |
| 21 | −7.5 ± 4.2 | −7.0 ± 3.4 | −1.5 ± 1.2 | 11.9 ± 4.8 |
| 36 | 9.7 ± 1.8 | 43.5 ± 0.5 | 2.7 ± 0.7 | 40.0 ± 3.5 |
| 69 | 4.2 ± 6.3 | 54.8 ± 9.3 | 15.6 ± 4.0 | 89.8 ± 0.8 |
| 74 | −10.2 ± 1.4 | 24.5 ± 3.3 | 18.7 ± 2.8 | 73.0 ± 0.3 |
| 75 | −8.0 ± 2.0 | 64.5 ± 6.4 | 32.3 ± 2.4 | 79.0 ± 1.8 |
| 76 | −4.8 ± 4.1 | −17.2 ± 0.9 | 5.3 ± 3.9 | 34.1 ± 2.5 |
| 77 | 8.4 ± 0.4 | 2.5 ± 2.8 | 8.7 ± 2.3 | 24.3 ± 1.7 |
| 78 | 13.5 ± 5.6 | 7.6 ± 2.1 | 13.2 ± 1.4 | 51.3 ± 2.7 |
| 80 | −7.0 ± 0.8 | 22.1 ± 0.7 | −1.3 ± 3.4 | 56.2 ± 2.4 |
| 81 | −3.9 ± 1.5 | 7.3 ± 7.2 | 3.9 ± 2.2 | 73.4 ± 3.3 |
| 86 | −1.0 ± 11.2 | −4.3 ± 1.9 | 19.8 ± 7.0 | 78.7 ± 0.7 |
| 87 | 3.7 ± 3.3 | 35.5 ± 4.2 | 30.3 ± 3.8 | 86.2 ± 0.6 |

Each value represents mean ± standard deviation.

As shown in Table 11, the compounds of the present invention inhibit cell injury induced by oxidized LDL.

Test Example 4
Effect on Puromycin-Induced Nephrosis (1) (in vivo)

Effect of the compound of the present invention on an in vivo renal disease was studied using a puromycin-induced nephrosis model.

A puromycin-induced renal failure model was prepared from rats in groups of 5–8 each (6 week-old male SD rats) fed with high-fat diet. High-fat diet feeding was started by free access to high-fat diet (cholesterol level 1.25%) from 7 days before puromycin treatment. Puromycin (puromycin aminonucleoside, SIGMA Chemical Co.) treatment was performed by intraperitoneal administration at a dose of 100 mg/kg. The test compound was administered as a solution in soybean oil via oral route (4 ml/kg). Control group was orally administered soybean oil alone. The administration of compound was started from 3 days before the puromycin treatment once a day. After the puromycin treatment, the oral administration of the compound was continued.

Renal functions were determined by using urine and blood samples collected on day 8 after the puromycin treatment. Volume of urine and the creatinine levels in serum and urine were evaluated to calculate creatinine clearance as an indication of renal functions.

The results are shown in Table 12.

TABLE 12

Effect of the compound of Example 36 on purimycin-induced renal dysfunction (preadministration)

|  | Creatinine (mg/dl) | Creatinine clearance (ml/day) |
|---|---|---|
| Control group (soybean oil) | 0.93 ± 0.21 | 576 ± 148 |
| 20 mg/kg | 0.71 ± 0.14 | 724 ± 176 |
| 200 mg/kg | 0.59 ± 0.23[a] | 1055 ± 482[a] |
| Normal group | 0.54 ± 0.03* | 1066 ± 172** |

Each value represents mean ± standard deviation.
[a]$P < 0.05$
*$P < 0.01$
**$P < 0.001$.

As shown in Table 12, a compound of the present invention shows an inhibitory effect against an increase of serum creatinine level and a decrease of creatinine clearance in a rat puromycin-induced renal failure model when the compound is administered before puromycin treatment.

Test Example 5

Effect on Puromycin-Induced Nephrosis (2) (in vivo)

Effect of the compounds of the present invention on an in vivo renal disease was studied using a puromycin-induced nephrosis model.

A puromycin-induced renal failure model was prepared from rats in groups of 5–8 each (6 week-old male SD rats) fed with high-fat diet. High-fat diet feeding was started by free access to high-fat diet (cholesterol level 1.25%) from 7 days before puromycin treatment. Puromycin (puromycin aminonucleoside, SIGMA Chemical Co.) treatment was performed by intraperitoneal administration at a dose of 100 mg/kg. Test compounds were administered as a solution in soybean oil via oral route (4 ml/kg). Control group was orally administered soybean oil alone. Probucol and a water-soluble α-tocopherol analogue, Trolox, were used as reference control compounds. The compounds were orally administered once a day from the following day of the puromycin treatment.

Renal functions were determined by using urine and blood samples. The volume of urine, urea nitrogen level and creatinine levels of serum and urine were evaluated to calculate creatinine clearance as an indication of renal functions.

The results are shown in Table 13.

TABLE 13

Effect of example compounds on puromycin-induced renal dysfunction (postadministration)

|  | Urine nitrogen (mg/dl) | Creatinine (mg/dl) | Creatinine clearance (ml/day) |
|---|---|---|---|
| Normal group | 14.78 ± 2.67[a] | 0.59 ± 0.08** | 1130 ± 208[a] |
| Control group (soybean oil) | 30.74 ± 10.95 | 0.82 ± 0.07 | 824 ± 108 |
| Compound of Example 16 (200 mg/kg) | 31.82 ± 10.84 | 0.73 ± 0.06[a] | 925 ± 140 |
| Compound of Example 20 (200 mg/kg) | 25.40 ± 10.28 | 0.61 ± 0.08** | 1144 ± 172* |
| Compound of Example 36 (200 mg/kg) | 24.57 ± 10.68 | 0.75 ± 0.11 | 837 ± 205 |
| Trolox (200 mg/kg) | 31.91 ± 11.93 | 0.96 ± 0.14[a] | 660 ± 104[a] |
| Probucol (200 mg/kg) | 37.53 ± 7.53 | 0.98 ± 0.13[a] | 838 ± 187 |

Each value represents mean ± standard deviation.
[a] $P < 0.05$
* $P < 0.01$
** $P < 0.001$.

As shown in Table 13, the compounds of the present invention show an inhibitory effect against an increase of serum creatinine level and a decrease of creatinine clearance by the administration after puromycin treatment in a rat puromycin-induced renal failure model.

Test Example 6

Effect on Ischemic Acute Renal Failure Model (in vivo)

Effect of a compound of the present invention on an in vivo renal disease was studied using an ischemic acute renal failure model.

An ischemic acute renal failure model was prepared from in groups of 8 each rats (male SD rats, weight: 224–285 g) fed with high-fat diet. High-fat diet feeding was started by free access to high-fat diet (cholesterol level 1.25%) from 7 or 8 days prior to unilateral nephrectomy and left renal artery clamping. The test compound was administered as a solution in soybean oil via oral route (4 ml/kg). Control group was orally administered soybean oil alone. The administration of compound was started from 4 or 5 days before the ischemic treatment at a dose of 200 mg/kg once a day. After the ischemia treatment, the oral administration of the compound was continued at a frequency of once a day. The ischemic treatment was performed by removing the right kidney and clipping a renal artery of the left kidney for 30 or 60 minutes.

Renal functions after ischemic treatment were determined by using urine and blood samples daily collected. Urine volume and the creatinine level of serum and urine were evaluated to calculate creatinine clearance as an indication of renal functions. Influences of high-fat diet feeding were monitored by measuring serum cholesterol level.

The results are shown in Tables 14 and 15.

TABLE 14

Effect of the compound of Example 36 on a renal ischemia (30 minutes) - induced acute renal failure model

|  | Days after ischemia | Creatinine (mg/dl) | Creatinine clearance (ml/day) |
|---|---|---|---|
| Control group (soybean oil) | 1 | 1.73 ± 0.73 | 632 ± 167 |
|  | 2 | 1.84 ± 1.40 | 678 ± 277 |
|  | 3 | 2.19 ± 2.34 |  |
| Compound of | 1 | 1.06 ± 0.24[a] | 934 ± 253[a] |

TABLE 14-continued

Effect of the compound of Example 36 on a renal ischemia (30 minutes) - induced acute renal failure model

| | Days after ischemia | Creatinine (mg/dl) | Creatinine clearance (ml/day) |
| --- | --- | --- | --- |
| Example 36 | 2 | 0.96 ± 0.23 | 1095 ± 325[a] |
| | 3 | 1.05 ± 0.26 | |

Each value represents mean ± standard deviation.
[a]$P < 0.05$.

TABLE 15

Effect of the compound of Example 36 on a renal ischemia (60 minutes) - induced acute renal failure model

| | Days after ischemia | Creatinine (mg/dl) | Creatinine clearance (ml/day) |
| --- | --- | --- | --- |
| Control group (soybean oil) | 1 | 3.89 ± 0.77 | 276 ± 118 |
| | 2 | 3.33 ± 1.90 | 363 ± 140 |
| | 3 | 3.19 ± 2.19 | |
| Compound of Example 36 | 1 | 2.81 ± 0.42* | 478 ± 171[a] |
| | 2 | 1.94 ± 0.30 | 594 ± 123* |
| | 3 | 1.86 ± 0.27 | |

Each value represents mean ± standard deviation.
[a]$P < 0.05$.
*$P < 0.01$.

As shown in Tables 14 and 15, a compound of the present invention shows an inhibitory effect against an increased of blood creatinine level and a decrease of creatinine clearance in a rat ischemic acute renal failure model.

Industrial Applicability of the Invention

Therapeutic agents for renal diseases and organ preservatives containing a 2,6-di-t-butylphenol derivative as an active ingredient according to the present invention exhibit a potent cytoprotective effect against cell injury induced by oxidized LDL in kidney-derived cells in culture as well as a potent improving effect on renal functions in puromycin-induced nephrosis and ischemic acute renal failure models, so that they are useful as therapeutic or preventive agents for renal diseases such as chronic renal failure, diabetic nephropathy, glomerular nephritis, immunocomplex nephritis, acute renal failure, nephropathies caused by platinum complex-based anticancer agents such as cisplatin or other drugs such as gentamicin, nephropathies caused by agrichemicals such as Paracort, uremia, etc. They are also useful as organ preservatives.

What is claimed is:

1. A method for the treatment of renal diseases comprising administering to a patient in need thereof an effective amount for said treatment of a therapeutic agent for renal diseases containing a compound represented by the general formula (1):

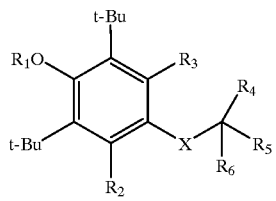

(1)

wherein X represents an oxygen atom or a group represented by the general formula (2):

(2)

where n represents an integer from 0 to 2,
$R_1$ represents a hydrogen atom or an acyl group,
$R_2$ represents a hydrogen atom, a lower alkyl group or a lower alkenyl group,
$R_3$ represents a lower alkyl group,
$R_4$, $R_5$ and $R_6$, which may be the same or different, each represents a hydrogen atom, an optionally substituted alkyl group, an optionally substituted alkenyl group, an optionally substituted alkynyl group or an optionally substituted aryl group, or $R_6$ further represents a formyl group, a carboxyl group, a lower alkoxycarbonyl group or an optionally substituted carbamoyl group, or
$R_3$ and $R_4$ may be taken together to form a five-membered ring, or
$R_5$ and $R_6$ may be taken together to form a cycloalkyl group or a saturated heterocyclic group containing one or more oxygen atoms, sulfur atoms or alkyl-substituted nitrogen atoms,
provided than when the five-membered ring formed by $R_3$ and $R_4$ and the benzene ring taken together to form benzofuran, benzo[b]thiophene, benzo[b]thiophene-1-oxide or benzo[b]thiophene-1,1-dioxide, $R_6$ is absent, or an optically active isomer or a pharmaceutically acceptable salt thereof as an active ingredient.

2. The method of claim 1, wherein the compound represented by the general formula (1) is selected from compounds represented by the general formula (3):

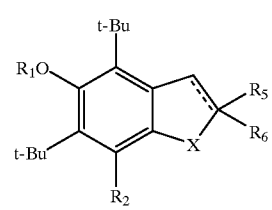

(3)

wherein X represents an oxygen atom or a group represented by the general formula (2):

(2)

where n represents an integer from 0 to 2,
$R_1$ represents a hydrogen atom or an acyl group,
$R_2$ represents a hydrogen atom, a lower alkyl group or a lower alkenyl group,
$R_5$ and $R_6$, which may be the same or different, each represents a hydrogen atom, an optionally substituted alkyl group, an optionally substituted alkenyl group, an optionally substituted alkynyl group or an optionally substituted aryl group, or $R_6$ further represents a formyl group, a carboxyl group, a lower alkoxycarbonyl group or an optionally substituted carbamoyl group, or
$R_5$ and $R_6$ may be taken together to form a cycloalkyl group or a saturated heterocyclic group containing one or more oxygen atoms, sulfur atoms or alkyl-substituted nitrogen atoms,
provided that when the bicyclic ring containing X is benzofuran, benzo[b]thiophene, benzo[b]thiophene-1-oxide or benzo[b]thiophene-1,1-dioxide, $R_6$ is absent.

3. The method of claim 1, wherein, $R_4$, $R_5$ and $R_6$ in the general formula (1), which may be the same or different, each represents a hydrogen atom, an optionally substituted alkyl group, an optionally substituted alkenyl group, an optionally substituted alkynyl group or an optionally substituted aryl group.

4. The method of claim 2, wherein, $R_4$, $R_5$ and $R_6$ in the general formula (3), which may be the same or different, each represents a hydrogen atom, an optionally substituted alkyl group, an optionally substituted alkenyl group, an optionally substituted alkynyl group or an optionally substituted aryl group.

5. The method of claim 1, wherein the compound represented by the general formula (1) is selected from the group consisting of compounds represented by the general formula (4):

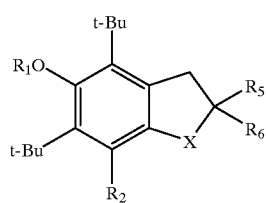

(4)

wherein X represents an oxygen atom or a sulfur atom, $R_1$ represents a hydrogen atom or an acyl group, $R_2$ represents a hydrogen atom, a lower alkyl group or a lower alkenyl group, $R_5$ and $R_6$, which may be the same or different, each represents a hydrogen atom, an optionally substituted alkyl group having 1 to 20 carbon atoms, an optionally substituted alkenyl group having 2 to 20 carbon atoms, an optionally substituted alkynyl group having 2 to 20 carbon atoms or an optionally substituted aryl group, or $R_6$ further represents a formyl group, a carboxyl group, a lower alkoxycarbonyl group or an optionally substituted carbamoyl group, or $R_5$ and $R_6$ may be taken together to form a cycloalkyl group or a saturated heterocyclic group containing one or more oxygen atoms, sulfur atoms or alkyl-substituted nitrogen atoms.

6. The method of claim 5, wherein, in the general formula (4),

X represents an oxygen atom or a sulfur atom, $R_1$ represents a hydrogen atom or an acyl group, $R_2$ represents a hydrogen atom, a lower alkyl group or a lower alkenyl group, $R_5$ represents a hydrogen atom, an optionally substituted alkyl group having 1 to 20 carbon atoms, an optionally substituted alkenyl group having 2 to 20 carbon atoms, an optionally substituted alkynyl group having 2 to 20 carbon atoms or an optionally substituted aryl group, and $R_6$ represents (i) a formyl, carboxyl, lower alkoxycarbonyl, carbamoyl, mono- or di-lower alkyl-substituted carbamoyl, pyrrolydinocarbonyl, piperidinocarbonyl, piperazinocarbonyl or morpholinocarbonyl group, (ii) an alkyl group having 1 to 20 carbon atoms substituted by one or more substituents selected from the group consisting of cyano, carboxyl, lower alkoxycarbonyl, carbamoyl, mono- or di-lower alkyl-substituted carbamoyl, pyrrolydinocarbonyl, piperidinocarbonyl, piperazinocarbonyl and morpholinocarbonyl groups, or (iii) an alkenyl group having 2 to 20 carbon atoms substituted by one or more substituents selected from the group consisting of cyano, carboxyl, lower alkoxycarbonyl, carbamoyl, mono- or di-lower alkyl-substituted carbamoyl, pyrrolydinocarbonyl, piperidinocarbonyl, piperazinocarbonyl and morpholinocarbonyl groups.

7. The method of claim 6, wherein, in the general formula (4),

X represents an oxygen atom, $R_1$ represents a hydrogen atom or an acyl group, and $R_2$ represents a hydrogen atom or a lower alkyl group.

8. The method of claim 6, wherein, in the general formula (4),

X represents a sulfur atom, $R_1$ represents a hydrogen atom or an acyl group, and $R_2$ represents a hydrogen atom or a lower alkyl group.

9. The method of claim 5, wherein, in the general formula (4),

X represents an oxygen atom or a sulfur atom, $R_1$ represents a hydrogen atom or an acyl group, $R_2$ represents a hydrogen atom, a lower alkyl group or a lower alkenyl group, and $R_5$ and $R_6$, which may be the same or different, each represents a hydrogen atom, an optionally substituted alkyl group having 1 to 20 carbon atoms, an optionally substituted alkenyl group having 2 to 20 carbon atoms, an optionally substituted alkynyl group having 2 to 20 carbon atoms or an optionally substituted aryl group, or $R_5$ and $R_6$ may be taken together to form a cycloalkyl group or a saturated heterocyclic group containing one or more oxygen atoms, sulfur atoms or alkyl-substituted nitrogen atoms.

10. The method of claim 9, wherein, in the general formula (4),

X represents an oxygen atom, $R_1$ represents a hydrogen atom, and $R_2$ represents a hydrogen atom or a lower alkyl group.

11. The method of claim 9, wherein, in the general formula (4)

X represents a sulfur atom, $R_1$ represents a hydrogen atom, and $R_2$ represents a hydrogen atom or a lower alkyl group.

12. The method of claim 9, wherein, in the general formula (4),

X represents an oxygen atom or a sulfur atom, $R_1$ represents a hydrogen atom or an acyl group, $R_2$ represents a hydrogen atom, a lower alkyl group or a lower alkenyl group, $R_5$ represents a hydrogen atom, an optionally substituted alkyl group having 1 to 20 carbon atoms, an optionally substituted alkenyl group having 2 to 20 carbon atoms, an optionally substituted alkynyl group having 2 to 20 carbon atoms or an optionally substituted aryl group, and $R_6$ represents (i) an alkyl group having 1 to 20 carbon atoms substituted by one or more substituents selected from the group consisting of thioureido, 3-aminoguanidino, N-guanidinoamino, 4-guanidinophenoxy and 4-(N-guanidinoaminomethyl) phenoxy groups, or (ii) an alkenyl group having 2 to 20 carbon atoms substituted by one or more substituents selected from the group consisting of thioureido, 3-aminoguanidino, N-guanidinoamino, 4-guanidinophenoxy and 4-(N-guanidinoaminomethyl) phenoxy groups.

13. The method of claim 12, wherein, in the general formula (4),

X represents an oxygen atom,

R₁ represents a hydrogen atom or an acyl group, and

R₂ represents a hydrogen atom or a lower alkyl group.

14. The method of claim 12, wherein, in the general formula (4),

X represents a sulfur atom,

R₁ represents a hydrogen atom or an acyl group, and

R₂ represents a hydrogen atom or a lower alkyl group.

15. The method of claim 1, wherein the renal disease is selected from the group consisting of chronic renal failure, diabetic nephropathy, glomerular nephritis, immunocomplex nephritis, acute renal failure, nephropathies caused by platinum complex-based anticancer agents or other drugs, nephropathies caused by agrichemicals and uremia.

16. The method of claim 2, wherein the renal disease is selected from the group consisting of chronic renal failure, diabetic nephropathy, glomerular nephritis, immunocomplex nephritis, acute renal failure, nephropathies caused by platinum complex-based anticancer agents or other drugs, nephropathies caused by agrichemicals and uremia.

17. The method of claim 5, wherein the renal disease is selected from the group consisting of chronic renal failure, diabetic nephropathy, glomerular nephritis, immunocomplex nephritis, acute renal failure, nephropathies caused by platinum complex-based anticancer agents or other drugs, nephropathies caused by agrichemicals and uremia.

18. The method of claim 6, wherein the renal disease is selected from the group consisting of chronic renal failure, diabetic nephropathy, glomerular nephritis, immunocomplex nephritis, acute renal failure, nephropathies caused by platinum complex-based anticancer agents, nephropathies caused by agrichemicals and uremia.

19. The method of claim 10, wherein the renal disease is selected from the group consisting of chronic renal failure, diabetic nephropathy, glomerular nephritis, immunocomplex nephritis, acute nephritis, nephropathies caused by platinum complex-based anticancer agents or other drugs, nephropathies caused by agrichemicals and uremia.

20. In a method of perfusing an animal organ or maintaining said animal organ in a bath of a maintenance solution to minimize damage thereof during storage of said organ extracted from a donor for transplantation, said method comprising perfusing said organ with a perfusion solution or storing said extracted organ in a maintenance solution, the improvement wherein said solution contains an organ-protective amount of a compound of formula (1):

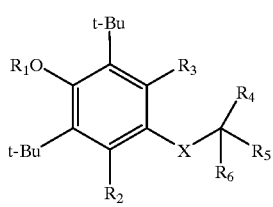

(1)

wherein X represents an oxygen atom or a group represented by the general formula (2):

(2)

where n represents an integer from 0 to 2,

R₁ represents a hydrogen atom or an acyl group,

R₂ represents a hydrogen atom, a lower alkyl group or a lower alkenyl group,

R₃ represents a lower alkyl group,

R₄, R₅ and R₆, which may be the same or different, each represents a hydrogen atom, an optionally substituted alkyl group, an optionally substituted alkenyl group, an optionally substituted alkynyl group or an optionally substituted aryl group, or R₆ further represents a formyl group, a carboxyl group, a lower alkoxycarbonyl group or an optionally substituted carbamoyl group, or R₃ and R₄ may be taken together to form a five-membered ring, or R₅ and R₆ may be taken together to form a cycloalkyl group or a saturated heterocyclic group containing one or more oxygen atoms, sulfur atoms or alkyl-substituted nitrogen atoms, provided than when the five-membered ring formed by R₃ and R₄ and the benzene ring taken together to form benzofuran, benzo[b]thiophene, benzo[b]thiophene-1-oxide or benzo[b]thiophene-1,1-dioxide, R₆ is absent, or an optically active isomer or a pharmaceutically acceptable salt thereof as an active ingredient.

21. The method of claim 20 wherein said compound is represented by the formula (3):

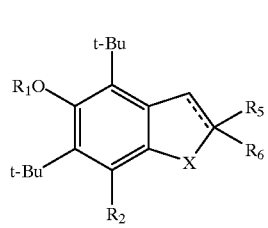

(3)

wherein X represents an oxygen atom or a group represented by the general formula (2):

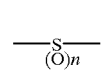

(2)

where n represents an integer from 0 to 2,

R₁ represents a hydrogen atom or an acyl group,

R₂ represents a hydrogen atom, a lower alkyl group or a lower alkenyl group,

R₅ and R₆, which may be the same or different, each represents a hydrogen atom, an optionally substituted alkyl group, an optionally substituted alkenyl group, an optionally substituted alkynyl group or an optionally substituted aryl group, or R₆ further represents a formyl group, a carboxyl group, a lower alkoxycarbonyl group or an optionally substituted carbamoyl group, or R₅ and R₆ may be taken together to form a cycloalkyl group or a saturated heterocyclic group containing one or more oxygen atoms, sulfur atoms or alkyl-substituted nitrogen atoms, provided than when the bicyclic ring containing X is bensofuran, benzo[b]thiophene, benzo[b]thiophene-1-oxide or benzo[b]thiophene-1,1-dioxide, R₆ is absent.

22. The method of claim 20 wherein said compound is represented by the formula (4):

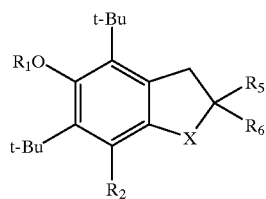

(4)

wherein

X represents an oxygen atom or a sulfur atom, $R_1$ represents a hydrogen atom or an acyl group, $R_2$ represents a hydrogen atom, a lower alkyl group or a lower alkenyl group, $R_5$ and $R_6$, which may be the same or different, each represents a hydrogen atom, an optionally substituted alkyl group having 1 to 20 carbon atoms, an optionally substituted alkenyl group having 2 to 20 carbon atoms, an optionally substituted alkynyl group having 2 to 20 carbon atoms or an optionally substituted aryl group, or $R_6$ further represents a formyl group, a carboxyl group, a lower alkoxycarbonyl group or an optionally substituted carbamoyl group, or $R_5$ and $R_6$ may be taken together to form a cycloalkyl group or a saturated heterocyclic group containing one or more oxygen atoms, sulfur atoms or alkyl-substituted nitrogen atoms.

23. The method of claim 22 wherein

X represents an oxygen atom or a sulfur atom, $R_1$ represents a hydrogen atom or an acyl group, $R_2$ represents a hydrogen atom, a lower alkyl group or a lower alkenyl group, $R_5$ represents a hydrogen atom, an optionally substituted alkyl group having 1 to 20 carbon atoms, an optionally substituted alkenyl group having 2 to 20 carbon atoms, an optionally substituted alkynyl group having 2 to 20 carbon atoms or an optionally substituted aryl group, and $R_6$ represents (i) a formyl, carboxyl, lower alkoxycarbonyl, carbamoyl, mono- or di-lower alkyl-substituted carbamoyl, pyrrolydinocarbonyl, piperidinocarbonyl, piperazinocarbonyl or morpholinocarbonyl group, (ii) an alkyl group having 1 to 20 carbon atoms substituted by one or more substituents selected from the group consisting of cyano, carboxyl, lower alkoxycarbonyl, carbamoyl, mono- or di-lower alkyl-substituted carbamoyl, pyrrolydinocarbonyl, piperidinocarbonyl, piperazinocarbonyl and morpholinocarbonyl groups, or (iii) an alkenyl group having 2 to 20 carbon atoms substituted by one or more substituents selected from the group consisting of cyano, carboxyl, lower alkoxycarbonyl, carbamoyl, mono- or di-lower alkyl-substituted carbamoyl, pyrrolydinocarbonyl, piperidinocarbonyl, piperazinocarboyl and morpholinocarbonyl groups.

24. The method of claim 20 wherein said compound is represented by formula (4)

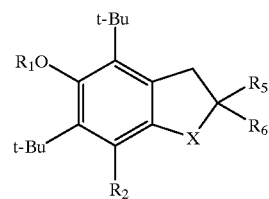

(4)

wherein

X represents an oxygen atom, $R_1$ represents a hydrogen atom, $R_2$ represents a hydrogen atom or a lower alkyl group, and $R_5$ and $R_6$, which may be the same or different, each represents a hydrogen atom, an optionally substituted alkyl group having 1 to 20 carbon atoms, an optionally substituted alkenyl group having 2 to 20 carbon atoms, an optionally substituted alkynyl group having 2 to 20 carbon atoms or an optionally substituted aryl group, or $R_5$ and $R_6$ may be taken together to form a cycloalkyl group or a saturated heterocyclic group containing one or more oxygen atoms, sulfur atoms or alkyl-substituted nitrogen atoms.

25. The method of claim 20 carried out in a method for renal transplantation.

26. The method of claim 21 carried out in a method of renal transplantation.

27. The method of claim 22 carried out in a method of renal transplantation.

28. The method of claim 23 carried out in a method of renal transplantation.

29. The method of claim 24 carried out in a method of renal transplantation.

30. A compound represented by the general formula (4)

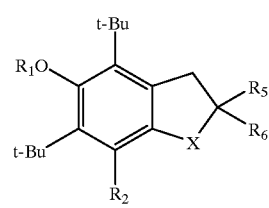

(4)

wherein X represents an oxygen atom or a sulfur atom, $R_1$ represents a hydrogen atom or an acyl group, $R_2$ represents a hydrogen atom, a lower alkyl group or a lower alkenyl group, $R_5$ represents a hydrogen atom, an optionally substituted alkyl group having 1 to 20 carbon atoms, an optionally substituted alkenyl group having 2 to 20 carbon atoms, an optionally substituted alkynyl group having 2 to 20 carbon atoms or an optionally substituted aryl group, and $R_6$ represents (i) a formyl, carboxyl, lower alkoxycarbonyl, carbamoyl, mono- or di-lower alkyl-substituted carbamoyl, pyrrolydinocarbonyl, piperidinocarbonyl, piperazinocarbonyl or morpholinocarbonyl group, (ii) an alkyl group having 1 to 20 carbon atoms substituted by one or more substituents selected from the groups consisting of cyano, carboxyl, lower alkoxycarbonyl, carbamoyl, mono- or di-lower alkyl-substituted carbamoyl, pyrrolydinocarbonyl, piperidinocarbonyl, piperazinocarbonyl and morpholinocarbonyl groups, or (iii) an alkenyl group having 2 to 20 carbon atoms substituted by one or more substituents selected from the group consisting of cyano, carboxyl, lower alkoxycarbonyl, carbamoyl, mono- or di-lower alkyl-substituted carbamoyl, pyrrolydinocarbonyl, piperidinocarbonyl, piperazinocarbonyl and morpholinocarbonyl groups provided that when X is oxygen, $R_1$ is acetyl and $R_5$ is methyl then $R_6$ is not butenyl which is substituted by lower alkoxycarbonyl, or an optically active isomer or a pharmaceutically acceptable salt thereof.

31. The compound of claim 30, wherein

X represents an oxygen atom, $R_1$ represents a hydrogen atom or an acyl group, and $R_2$ represents a hydrogen atom or a lower alkyl group, or an optically active isomer or a pharmaceutically acceptable salt thereof.

32. The compound of claim 30, wherein

X represents a sulfur atom, $R_1$ represents a hydrogen atom or an acyl group, and $R_2$ represents a hydrogen atom or a lower alkyl group or an optically active isomer or a pharmaceutically acceptable salt thereof.

33. A compound represented by the general formula (4):

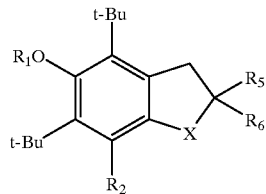

(4)

wherein X represents an oxygen atom or a sulfur atom, $R_1$ represents a hydrogen atom or an acyl group, $R_2$ represents a hydrogen atom, a lower alkyl group or a lower alkenyl group, $R_5$ represents a hydrogen atom, an optionally substituted alkyl group having 1 to 20 carbon atoms, an optionally substituted alkenyl group having 2 to 20 carbon atoms, an optionally substituted alkynyl group having 2 to 20 carbon atoms or an optionally substituted aryl group, and $R_6$ represents (i) an alkyl group having 1 to 20 carbon atoms substituted by one or more substituents selected from the group consisting of thioureido, 3-aminoguanidino, N-guanidinoamino, 4-guanidinophenoxy and 4-(N-guanidinoaminomethyl) phenoxy groups, or (ii) an alkenyl group having 2 to 20 carbon atoms substituted by one or more substituents selected from the group consisting of thioureido, 3-aminoguanidino, N-guanidinoamino, 4-guanidinophenoxy and 4-(N-guanidinoaminomethyl) phenoxy groups, or an optically active isomer or a pharmaceutically acceptable salt thereof.

34. The compound of claim 33, wherein

X represents an oxygen atom, $R_1$ represents a hydrogen atom or an acyl group, and $R_2$ represents a hydrogen atom or a lower alkyl group, or an optically active isomer or a pharmaceutically acceptable salt thereof.

35. The compound of claim 33, wherein

X represents a sulfur atom, $R_1$ represents a hydrogen atom or an acyl group, and $R_2$ represents a hydrogen atom or a lower alkyl group, or an optically active isomer or a pharmaceutically acceptable salt thereof.

36. A pharmaceutical composition comprising a therapeutically effective amount of a compound of claim 30 or a pharmaceutically acceptable salt thereof together with a pharmaceutical carrier therefor.

37. The composition of claim 36 wherein said composition is in a form adapted for use in treating a renal disease.

38. The composition of claim 36 wherein said composition is in a form adapted for use in preserving an organ.

* * * * *